United States Patent
Tsuchiya et al.

[11] Patent Number: 6,069,176
[45] Date of Patent: May 30, 2000

[54] PHENYLETHANOLAMINE COMPOUNDS USEFUL AS β 3 AGONISTS, PROCESS FOR PRODUCING THE SAME, AND INTERMEDIATES IN THE PRODUCTION OF THE SAME

[75] Inventors: Susumu Tsuchiya; Nobuyuki Yasuda; Toshifumi Matsumoto; Kozo Hiratsuka; Hiroyuki Iizuka; Atsusi Hukuzaki; Kouichi Matsunaga, all of Tokyo, Japan

[73] Assignee: Mitsubishi-Tokyo Pharmaceuticals, Inc., Japan

[21] Appl. No.: 09/065,077

[22] PCT Filed: Oct. 24, 1996

[86] PCT No.: PCT/JP96/03097

§ 371 Date: Apr. 24, 1998

§ 102(e) Date: Apr. 24, 1998

[87] PCT Pub. No.: WO97/15549

PCT Pub. Date: May 1, 1997

[30] Foreign Application Priority Data

Oct. 26, 1995 [JP] Japan .................... 7-278554
Sep. 20, 1996 [JP] Japan .................... 8-249622

[51] Int. Cl.[7] .............. A61K 31/135; C07C 49/255; C07C 49/753; C07C 213/02; C07C 217/74
[52] U.S. Cl. ................. 514/646; 514/656; 514/741; 514/866; 514/909; 564/305; 564/462
[58] Field of Search ............... 514/730, 741, 514/751, 754, 866, 892, 646, 656, 909; 564/305, 462

[56] References Cited

U.S. PATENT DOCUMENTS

| 3,803,232 | 4/1974 | Rodriguez et al. ............ 260/564 R |
| 4,350,685 | 9/1982 | Ali et al. ........................ 424/45 |
| 4,755,505 | 7/1988 | Winkley et al. .............. 514/183 |

FOREIGN PATENT DOCUMENTS

| 4210569 A1 | 10/1993 | Germany . |
| 47-27979 | 10/1972 | Japan . |
| 47-47376 | 11/1972 | Japan . |
| 49-40226 | 10/1974 | Japan . |
| 62-198639 | 9/1987 | Japan . |
| 1-135739 | 5/1989 | Japan . |
| 4-169595 | 6/1992 | Japan . |
| 4-211636 | 8/1992 | Japan . |
| 6-65107 | 3/1994 | Japan . |

OTHER PUBLICATIONS

Rosenbaum et al., "Lack of beta–3–Adreneric Effect on Lipolysis in Human Subcutaneous Adipose Tissue", Journal of Clinical Endocrinology and Metabolism, vol. 77: 352–355, 1993.
Airapetyan et al., Arm. Khim. Zh., 40(1): 40–44, 1987.
DeMeglio et al., "Sintesi E Studio Farmacologico Di Derivati Dell'Orciprenalina E Del Salbutamolo", Farmaco, Ed. Sci., vol. 35(3): 203–230, 1980.
Brouty–Boye, G. 1979, Chemical Abstracts vol. 93, 1980 p. 666.

*Primary Examiner*—Howard C. Lee
*Attorney, Agent, or Firm*—McGlew and Tuttle, P.C.

[57] ABSTRACT

The present invention relates to phenylethanolamine compounds represented by general formula [I]:

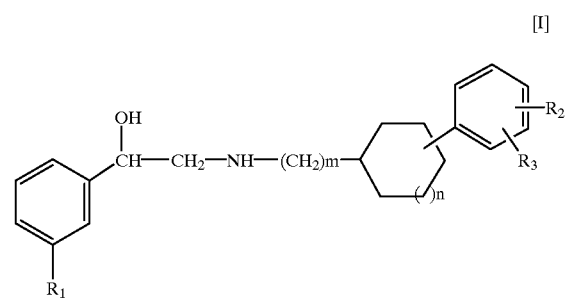

(where $R_1$ represents hydrogen or halogen; $R_2$ represents hydrogen, hydroxy, lower alkoxy, lower alkoxy substituted with one or two lower alkoxycarbonyl or carboxy groups, lower alkoxy substituted with lower alkylaminocarbonyl which may be substituted with lower alkoxy, lower alkoxy substituted with cyclic aminocarbonyl of 4 to 6 carbon atoms, lower alkoxycarbonyl or carboxy; $R_3$ represents hydrogen, hydroxy, lower alkoxy or lower alkoxy substituted with one or two lower alkoxycarbonyl or carboxy groups; $R_2$ and $R_3$ may be bonded to each other to form methylenedioxy substituted with carboxy or lower alkoxycarbonyl; and m and n are 0 or 1), and their pharmacologically acceptable salts, which have a potent β3 adrenergic stimulating effect and high β3 adrenergic receptor selectivity, as well as to processes for their production and intermediates in their production.

25 Claims, 2 Drawing Sheets

1

PHENYLETHANOLAMINE COMPOUNDS USEFUL AS β 3 AGONISTS, PROCESS FOR PRODUCING THE SAME, AND INTERMEDIATES IN THE PRODUCTION OF THE SAME

This application is a 371 of PCT/JP96/03097 filed on Oct. 24, 1996.

TECHNICAL FIELD OF THE INVENTION

The present invention relates to novel phenylethanolamine compounds with a β3 adrenergic receptor stimulating effect which are useful as drugs, and to their pharmacologically acceptable salts.

PRIOR ART

Sympathetic nerve β receptors include the subtypes β1, β2 and β3, among which it is believed that the β1 receptors are present mainly in the heart, and the β2 receptors are present in the trachea, uterus, bladder and vascular smooth muscle. Also, the β3 receptors are believed to be present on the cell surfaces of brown adipocytes and white adipocytes and in the enteric canal (Land, A. M. et al.: Nature, 214, 597–598 (1967). Emorine, L. J. et al.: Science, 245, 1118–1121 (1989)).

Current clinical applications of β1 adrenergic receptor agonists include their use as cardiac function promoters or vasopressors, and those of β2 adrenergic receptor agonists include their use as bronchial dilators, prophylactics against impending premature birth, or therapies for urinary incontinence. In addition, β3 adrenergic receptor agonists have been reported useful as antiobestic and antidiabetic drugs because they promote fat decomposition and energy consumption, and as therapies for accelerated gastrointestinal motility because they suppress it (J. Med. Chem. 35, 3081–3084 (1992). Br. J. Pharmacol. 100, 831–839 (1990)).

Drugs which are known to act selectively on β3 adrenergic receptors include 2-amino-1-phenylethanol compounds, such as BRL35135 [(R*R*)-(±)-[4-[2-[2-(3-chlorophenyl)-2-hydroxyethylamino]propyl]phenoxy]acetic acid methyl ester hydrobromide salt: Japanese Patent Publication No. 26744 of 1988 and European Patent Publication No. 23385], and SR58611A [(RS)-N-(7-ethoxycarbonylmethoxy-1,2,3,4-tetrahydronaphth-2-yl)-2-(3-chlorophenyl)-2-hydroxyethanamine hydrochloride: Japanese Laid-open Patent Publication No. 66152 of 1989 and European Laid-open Patent Publication No. 255415].

It has been reported that BRL35135 has a lypolytic and hypoglycemic effect while SR58611A has a potent suppressing effect on spontaneous locomotion of rat colon (Drugs of the Future, 18, 529–549 (1993)).

The β2 adrenergic receptor agonist clenbuterol hydrochloride acts directly on bladder detrusor muscle β2 receptors, having a relaxing effect on the bladder detrusor muscle (The autonomic nervous system, 26, 380–387 (1989)), and therefore finds clinical use as a therapy for urinary incontinence. However, there are problems associated with this treatment for urinary incontinence, because of side-effects including finger tremor and palpitation.

It is an object of the present invention to provide novel phenylethanolamine compounds and their pharmacologically acceptable salts, which have a strong β3 adrenergic stimulating effect and high β3 receptor selectivity, and which can be used as prophylactics and/or treatments for accelerated or spasmodic gastrointestinal motility, as well as obesity and diabetes, and pollakisuria; urinary incontinence and other forms of dysuria.

It is another object of the invention to provide a process for producing such phenylethanolamine compounds and their pharmacologically acceptable salts.

It is a further object of the invention to provide pharmaceutical compositions containing such phenylethanolamine compounds and their pharmacologically acceptable salts as active components thereof.

The present inventors have carried out diligent research aimed at discovering compounds which differ in chemical structure from the widely known β3 adrenergic agonists and which have a potent β3-selective β3 adrenergic receptor stimulating effect. As a result it was found that newly synthesized novel phenylethanolamine compounds satisfy these conditions. It was further found that these compounds of the invention have a potent relaxing effect on rat bladder detrusor muscle, and the present invention was thus completed.

DISCLOSURE OF THE INVENTION

The phenylethanolamine compounds of the invention are represented by general formula [I]:

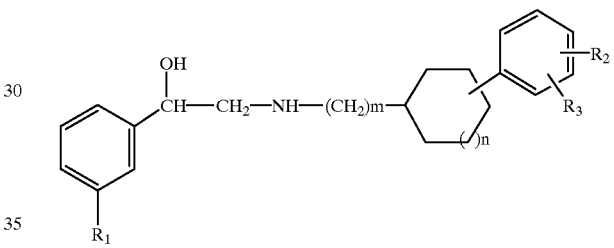

(where $R_1$ represents hydrogen or halogen; $R_2$ represents hydrogen, hydroxy, lower alkoxy, lower alkoxy substituted with one or two lower alkoxycarbonyl or carboxy groups, lower alkoxy substituted with lower alkylaminocarbonyl which may be substituted with lower alkoxy, lower alkoxy substituted with cyclic aminocarbonyl of 4 to 6 carbon atoms, lower alkoxycarbonyl or carboxy; $R_3$ represents hydrogen, hydroxy, lower alkoxy or lower alkoxy substituted with one or two lower alkoxycarbonyl or carboxy groups; $R_2$ and $R_3$ may be bonded to each other to form methylenedioxy substituted with carboxy or lower alkoxycarbonyl; and m and n are 0 or 1.)

In general formula [I] above, $R_1$ is preferably a halogen, such as fluorine, bromine, chlorine or iodine, and is most preferably chlorine. $R_2$ is preferably lower alkoxy substituted with one or two lower alkoxycarbonyl or carboxy groups, lower alkoxy substituted with a lower alkylaminocarbonyl group which may be substituted with lower alkoxy, or lower alkoxy substituted with a cyclic aminocarbonyl group of 4 to 6 carbon atoms, but it is most preferably methoxy substituted with one or two lower alkoxycarbonyl groups. As lower alkoxy groups for lower alkoxycarbonyl there may be mentioned methoxy, ethoxy, n-propoxy, iso-propoxy, n-butoxy and tert-butoxy, among which are preferred methoxy and ethoxy, especially ethoxy. $R_3$ is preferably hydrogen, and 1-phenyl-2-(3-phenylcyclohexylamino) ethanol compounds wherein m is 0 and n is 1 are particularly preferred.

Also, particularly preferred are compounds wherein the asymmetrical carbon atom to which the hydroxyl group is attached in the phenylethanolamine compound represented by general formula [I] has an absolute configuration (R) rather than compounds wherein it has an absolute configuration (S). As mentioned above, the compounds of the invention represented by general formula [I] also include their pharmacologically acceptable salts. Because the compounds of the invention [I] have 3 asymmetrical carbon atoms, they exist as 8 optical isomers. Mixtures of any two to all eight isomers in any proportion, as well as optically pure isomers, are all within the scope of the present invention. Furthermore, compounds wherein the hydroxyl-attached asymmetrical carbon atom has an absolute configuration (R) are particularly preferred, and in the case of 3-arylcyclohexylamines, the steric configuration of the asymmetrical carbon atom is preferably trans (R*R*).

Salts of the compounds of the invention [I] are not particularly restricted so long as they are pharmacologically acceptable salts, and examples thereof include salts with inorganic acids such as hydrochloric acid, nitric acid, sulfuric acid, hydrobromic acid, hydroiodic acid and phosphoric acid; salts with organic acids such as acetic acid, tartaric acid, fumaric acid, maleic acid, malic acid, methanesulfonic acid, ethanesulfonic acid, camphor-sulfonic acid, benzenesulfonic acid and toluenesulfonic acid; and salts with alkali metal or alkaline earth metal such as sodium, potassium and calcium. The present invention encompasses the compounds of the invention [I] as well as their pharmacologically acceptable salts and hydrates.

As particularly suitable compounds there may be mentioned the following and their pharmacologically acceptable salts.

(1R)-1-(3-chlorophenyl)-2-[(1R),(3R)-3-(3-ethoxycarbonylmethoxyphenyl)cyclohexylamino]ethanol,
(1R)-1-(3-chlorophenyl)-2-[(1S),(3S)-3-(3-ethoxycarbonylmethoxyphenyl)cyclohexylamino]ethanol,
(1R)-1-(3-chlorophenyl)-2-[(1R),(3R)-3-(3-carboxymethoxyphenyl) cyclohexylamino]ethanol, (1R)-1-(3-chlorophenyl)-2-[(1S),(3S)-3-(3-carboxymethoxyphenyl)cyclohexylamino]ethanol.

BEST MODE FOR CARRYING OUT THE INVENTION

Figure 1:
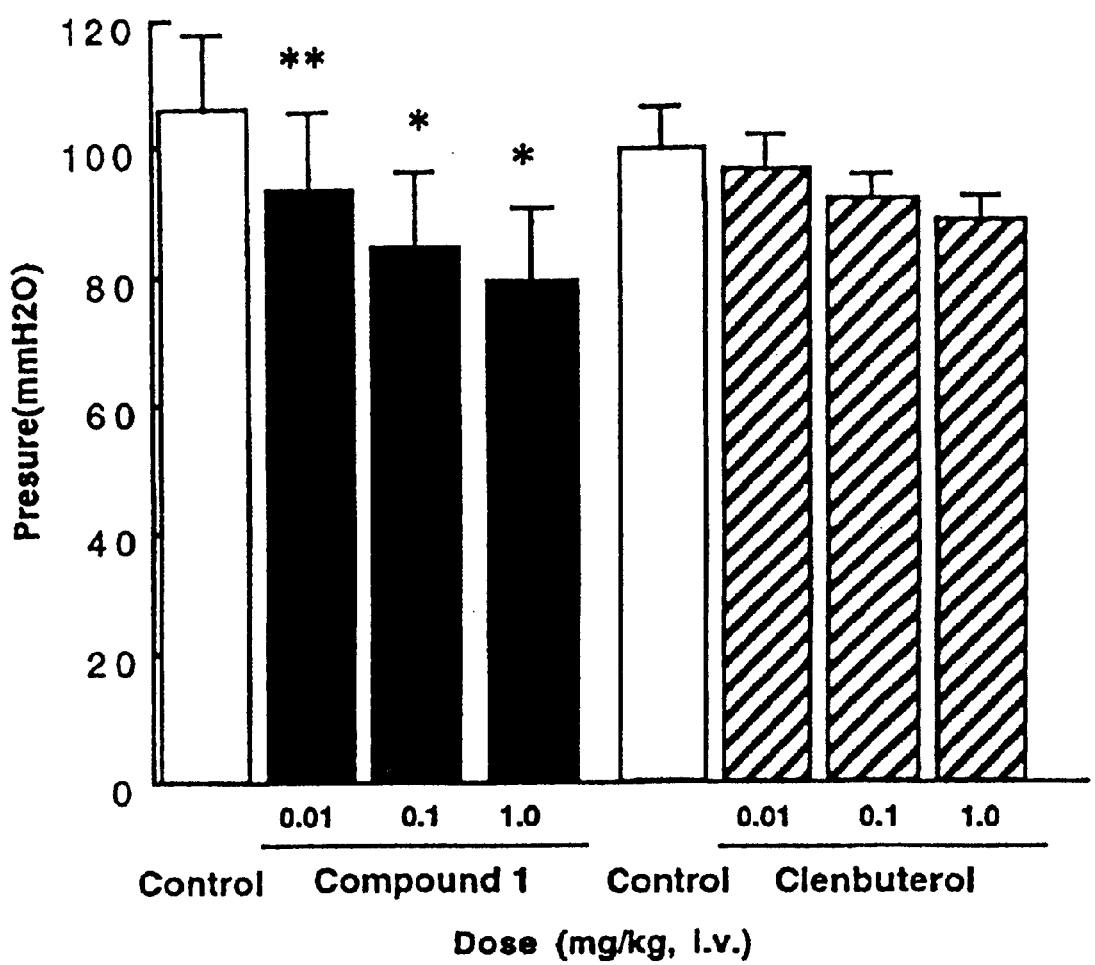
FIG. 1 is an illustration of the bladder relaxing effect of test compounds in anesthetized rats.

Compounds of the invention [I] maybe produced, for example, by the following processes.

Production process (a)

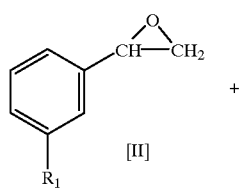

+

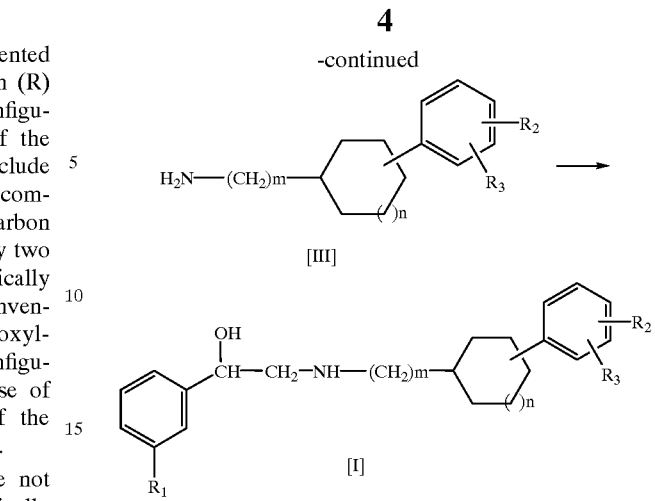

An addition reaction is carried out between a compound of formula [II] (where $R_1$ represents hydrogen or a halogen) and a compound of formula [III] (where $R_2$ represents hydrogen, hydroxy, lower alkoxy, lower alkoxy substituted with one or two lower alkoxycarbonyl or carboxy groups, lower alkoxy substituted with lower alkylaminocarbonyl which may be substituted with lower alkoxy, lower alkoxy substituted with cyclic aminocarbonyl of 4 to 6 carbon atoms, lower alkoxycarbonyl or carboxy; $R_3$ represents hydrogen, hydroxy, lower alkoxy or lower alkoxy substituted with one or two lower alkoxycarbonyl or carboxy groups; $R_2$ and $R_3$ may be bonded to each other to form methylenedioxy substituted with carboxy or lower alkoxycarbonyl; and m and n are 0 or 1), either in an appropriate solvent or without a solvent.

The solvent used may be an alcohol such as methanol, ethanol or isopropyl alcohol; a ketone such as acetone or methyl ethyl ketone; an ether such as diethyl ether, tetrahydrofuran or dioxane; a halogenated hydrocarbon such as methylene chloride or chloroform; an aromatic hydrocarbon such as benzene or toluene; or ethyl acetate, dimethylsulfoxide (abbreviated as DMSO), N,N-dimethylformamide (abbreviated as DMF), etc., with no particular restrictions and optionally in mixtures of 2 or more.

The reaction temperature is normally about 10 to 150° C., but is preferably about 50 to 100 ° C. The compounds of formula [III] can also be used in the form of acid addition salts, which acid addition salts may be inorganic acid salts such as hydrochlorides, hydrobromides, etc. or organic acid salts such as maleates, fumarates, etc. When an acid addition salt is used, the reaction is carried out in the presence of an alkali carbonate such as sodium carbonate or potassium carbonate, an alkali bicarbonate such as sodium bicarbonate or potassium bicarbonate, or an organic base such as triethylamine or N-methylmorpholine.

In this production process, when the starting compound has an asymmetrical carbon atom, the steric configuration with respect to the asymmetrical carbon atom is preserved in the compound of formula [I]. For example, a compound [II] with absolute configuration (R) and a compound [III] with (RR) will give a compound of the invention [I] (RRR) with the same steric configuration.

The RR form which is the optically active form of compound [III] can be obtained by optical resolution of the trans compound which is a mixture of 2 different diastereomers (mixture of RR and SS), using optically active mandelic acid or the like.

Production process (b)

A compound of formula [V] (where $R_1$, m and n have the same definitions given above, and $R_4$ and $R_5$ represent hydrogen, hydroxy or lower alkoxy) can be produced by reacting a compound of formula [IV] with a compound of formula [III'] in the presence of a condensation agent, an organic base and a solvent.

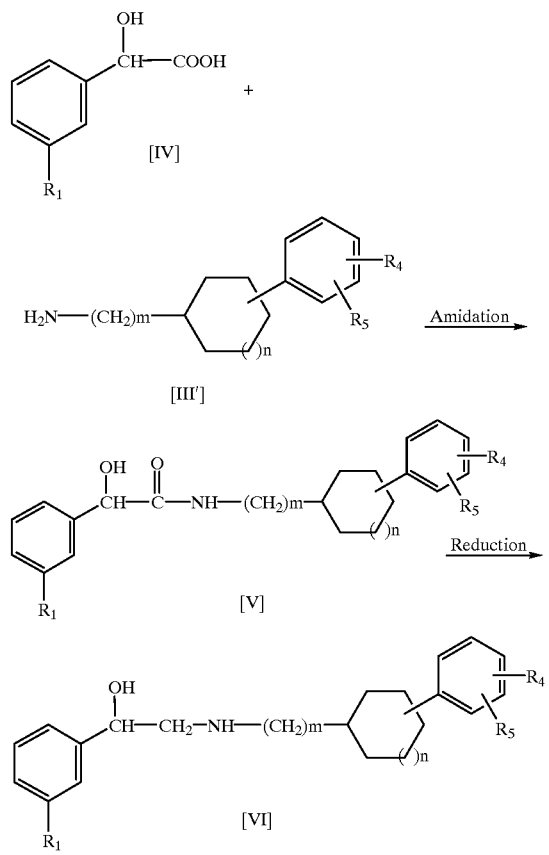

This reaction is carried out using any of various condensation agents in the presence of an organic base such as triethylamine, tributylamine or N-methyl morpholine and solvent. The condensation agent used may be one such as dicyclohexylcarbodiimide (hereunder abbreviated as DCC) or benzotriazol-1-yl-oxy-tris (dimethylamino) phosphonium hexafluorophosphate (hereunder abbreviated as BOP), and the reaction solvent used may be methylene chloride, ethyl acetate or the like, with no particular restrictions.

The reaction temperature is $-10$ to $70°$ C., and preferably 20 to $50°$ C. In this production process, when the mandelic acid compound of formula [IV], which is an (R) compound, is reacted with the amino compound of formula [III'], which is a trans compound (R*R*), the resulting amide compound of formula [V] is an (RR*R*) compound, so that the steric configuration with respect to the asymmetrical carbon atom is preserved. The (RR*R*) compound represents a mixture of the (RRR) compound and (RSS) compound, and each stereoisomer can be isolated and purified by common methods such as silica gel column chromatography and recrystallization.

The reaction for reduction of the amide compound of formula [V] is carried out under reducing conditions for the amide group, to allow production of a compound of formula [VI] (where $R_1$, $R_4$, $R_5$, m and n have the same definitions given above). The reducing agent used may be lithium aluminum hydride ($LiAlH_4$) or diborane ($B_2H_6$), and is preferably a borane-dimethylsulfide complex. The reaction solvent used may be a cyclic ether or linear ether, with the reaction preferably conducted in the presence of an aprotic solvent such as anhydrous tetrahydrofuran or dioxane, without any particular restrictions.

The reaction is carried out at room temperature (10 to $35°$ C.) or under reflux.

Production process (c)

A compound of formula [VI] (where $R_1$, m and n have the same definitions given above, and $R_4$ and $R_5$ represent hydrogen or methoxy) is treated with a demethylating agent such as boron tribromide ($BBr_3$), to produce a compound of formula [VII] (where $R_1$, m and n have the same definitions given above, and $R_6$ represents hydrogen or hydroxy). The reaction solvent used may be a halogen-based solvent such as methylene chloride or chloroform. The reaction is preferably conducted at a temperature of $-70$ to $30°$ C., and especially $-30$ to $20°$ C.

After preparing a compound of formula [VIII] (where $R_1$, $R_6$, m and n have the same definitions given above, and P represents a suitable N-protecting group) by protecting the amino group of formula [VII] with an appropriate protecting group, it is reacted with a compound of formula [IX] or formula [IX'] (where $R_7$ represents lower alkyl substituted with one or two lower alkoxycarbonyl groups, $R_8$ represents lower alkoxycarbonyl, and X represents an acid residue) for O-alkylation of the phenolic hydroxyl group of formula [VIII], after which deprotection produces a compound of formula [X] (where $R_1$, m and n have the same definitions given above, $R_9$ represents lower alkoxy substituted with one or two lower alkoxycarbonyl groups, $R_{10}$ represents hydrogen or lower alkoxy substituted with one or two lower alkoxycarbonyl groups, and $R_9$ and $R_{10}$ may be bonded to each other to form methylenedioxy substituted with lower alkoxycarbonyl).

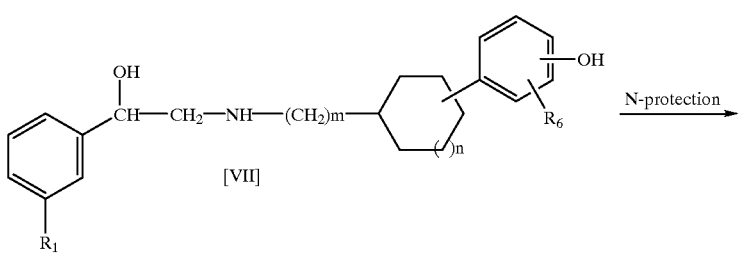

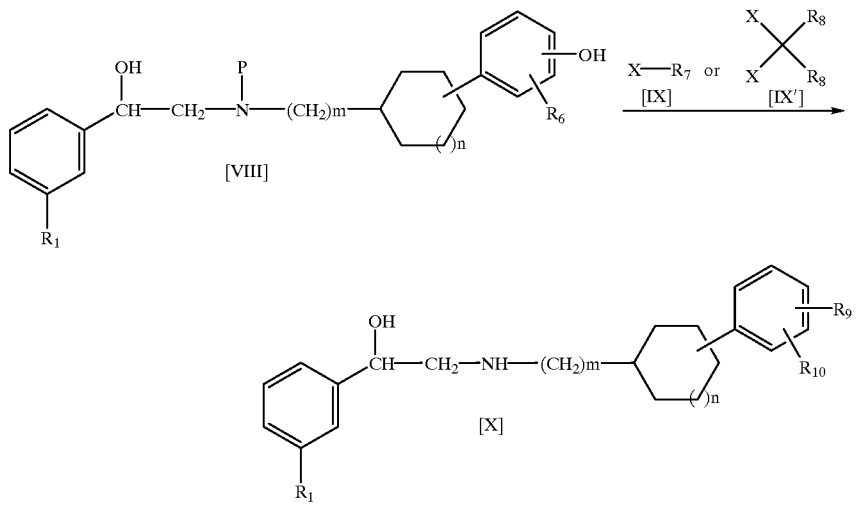

As suitable N-protecting groups there may be mentioned tert-butoxycarbonyl (Boc), benzyloxycarbonyl (Z) and benzyl or trityl groups which may be substituted with p-methoxy groups, but there are no particular restrictions. The alkylation is carried out in the presence of an alkali metal carbonate such as anhydrous potassium carbonate as the base, for example at a temperature in the range of 0 to 120° C. The reaction solvent used may be acetone, methyl ethyl ketone, DMF or the like, with no particular restrictions.

As suitable acid residues there may be mentioned halogens, mesyl and arenesulfonyloxy (for example, benzenesulfonyloxy, tosyloxy, etc.), but halogens (chlorine, bromine, iodine) are particularly preferred. The N-protecting group is removed by mild acid hydrolysis, using any method described in the publicly known literature. In particular, Boc groups can be easily removed off under acidic conditions by the action of trifluoroacetic acid or hydrogen chloride in an organic solvent, to produce compounds of formula [X].

Production process (d)

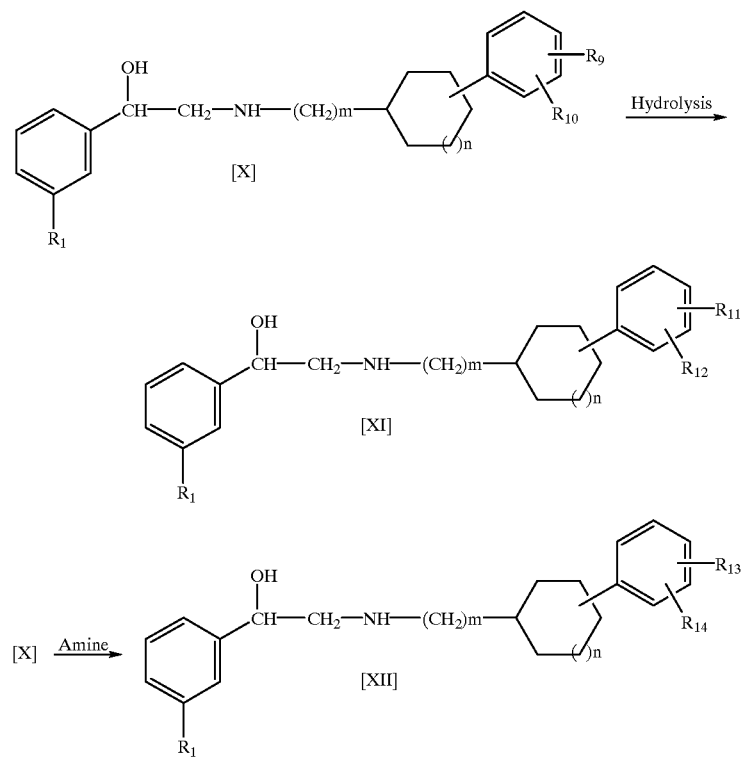

A compound of formula [X] (where $R_1$, $R_9$, $R_{10}$, m and n have the same definitions given above) can be hydrolyzed in hydrous alcohol using sodium hydroxide or potassium hydroxide to produce a compound of formula [XI] (where $R_1$, m and n have the same definitions given above, $R_{11}$ represents lower alkoxy substituted with one or two carboxy groups, $R_{12}$ represents hydrogen or lower alkoxy substituted with one or two carboxy groups, and $R_{11}$ and $R_{12}$ may be bonded to each other to form methylenedioxy substituted with carboxy).

Also, when a lower alkylamine or cyclic amine of 4 to 6 carbon atoms substituted with lower alkoxy is added to a compound of formula [X] (where $R_1$, m and n have the same definitions given above, $R_9$ represents lower alkoxy substituted with one or two lower alkoxycarbonyl groups, and $R_{10}$ represents hydrogen) for reaction, there may be produced a compound of formula [XII] (where $R_1$, m and n have the same definitions given above, $R_{13}$ represents lower alkoxy substituted with a lower alkylaminocarbonyl group which may be substituted with one or two lower alkoxy groups or lower alkoxy substituted with a cyclic aminocarbonyl group of 4 to 6 carbon atoms, and $R_{14}$ represents hydrogen) in which the ester is converted to an amide. The reaction may be carried out using chloroform, ethyl acetate, methylene chloride, DMF or the like, or it may be conducted in the absence of solvents, with addition of an excess of the amine. The reaction temperature is not particularly restricted, and may be room temperature or heating from 40 to 80° C.

A compound of formula [XII] can also be produced by reacting a compound of formula [XI] with an amine in the presence of any of various condensation agents. DCC or BOP may be used as the condensation agent and methylene chloride or ethyl acetate may be used as the reaction solvent, but there are no particular restrictions. The reaction temperature is −10 to 70° C., but is preferably 20 to 50° C.

Production process (e)

A compound of formula [I] (where $R_1$, $R_2$, $R_3$ and n have the same definitions given above, and m is 0) may be produced by first producing a compound of formula [XV] from a compound of formula [XIII] and a compound of formula [XIV], and then reacting the product under reducing conditions.

To produce a compound of formula [XV], a catalytic amount of p-toluenesulfonic acid is added in an aromatic hydrocarbon solvent such as benzene or toluene, and the reaction is conducted using a Dean-Stark like apparatus, while removing the generated water. The reaction temperature is normally from about 80 to 130° C.

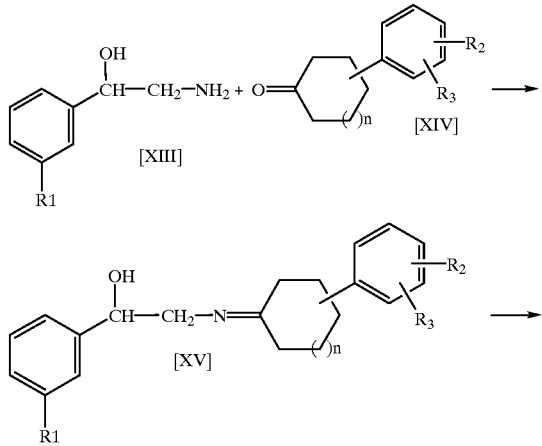

The reaction for reduction of the compound of formula [XV] is carried out under reducing conditions which can reduce the imine portion. Reducing conditions according to the present invention means in the presence of a reducing agent which can reduce the imine portion without affecting the carbonyl group, or catalytic hydrogen reducing conditions. Examples of reducing agents which can reduce imine portions include sodium cyanoborohydride and sodium borohydride. The reaction is carried out in an appropriate solvent, and the solvent used maybe an alcohol such as methanol, ethanol or isopropyl alcohol. The reaction temperature is normally about 0 to 100° C., and preferably 10 to 30° C.

When this production process is conducted under catalytic hydrogen reducing conditions, palladium-carbon, Raney nickel, platinum oxide or the like may be used as the catalyst. The solvent used may be an alcohol such as methanol, ethanol or isopropyl alcohol, or acetic acid or a mixed solvent of alcohol and acetic acid, and the reaction temperature is normally 0 to 100° C., preferably 30 to 60° C. A compound of formula [I] may also be directly produced by catalytic hydrogen reduction reaction from a compound of formula [XIII] and a compound of formula [XIV]. The reducing conditions used for this production process may be the same as the reduction conditions described above.

(Production process for intermediate 3-phenylcyclohexylamino compound)

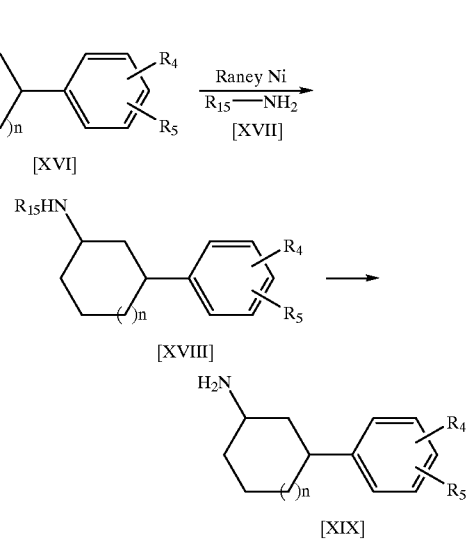

A compound of formula [XVI] may be subjected to catalytic hydrogen reduction in the presence of a compound of formula [XVII] and Raney nickel, to produce a compound of formula [XVIII] (where each $R_4$ and $R_5$ in the above formula have the same definitions given previously, $R_{15}$ represents lower alkyl substituted with an aryl group, and n is 1) or a salt thereof.

This reducing alkylation reaction is carried out in an alcohol such as methanol, ethanol, isopropyl alcohol or 1-butanol, with hydrogen addition under normal pressure or pressurization, and the reaction temperature is normally 0 to 100° C., and preferably 30 to 60° C.

If the reducing alkylation reaction is carried out under normal pressure or pressurization, it is possible to produce a compound of formula [XVIII] or its salt in the form of a trans-cis mixture, but hydrogen addition in the presence of Raney nickel gives predominantly the trans form.

As lower alkylamines substituted with aryl groups there may be mentioned diphenylmethylamine, phenylethylamine and naphthylethylamine, among which optically active phenylethylamine is preferred.

A compound of formula [XVIII] may be again subjected to hydrogen addition in the presence of a reducing agent to produce a compound of formula [XIX] or its pharmacologically acceptable salt. The reducing agent catalyst used may be palladium-carbon, platinum oxide or the like, with no particular restrictions.

The solvent used may be an alcohol such as methanol, ethanol or isopropyl alcohol, or acetic acid or a mixed solvent of alcohol and acetic acid, and the reaction temperature is normally 0 to 100° C., preferably 10 to 60° C.

The amine of formula [III] obtained in racemic form can be easily separated into its optically active forms by forming diastereomeric salts according to common methods and techniques, using appropriately selected optically active acids.

An optical isomer separating column may also be used for their separation. Even with compounds of formula [I], it is possible to separate all 8 optical isomers using an optical isomer separating column.

The characteristic effects of compounds of the invention will now be explained, referring to pharmacological test results for the compounds of the invention and known i adrenergic receptor agonists.

[Pharmacological Effects]

[Test 1] β3 adrenergic receptor stimulating effect

Isolated rat colon strips were used to examine the suppressing effect on spontaneous locomotion. Rat colons (about 3 cm downward from the ileocecum) were removed to prepare the strips. The strips were mounted in an organ bath filled with a nutrient medium (Krebs buffer, containing 0.03 mm ascorbic acid, 0.03 mM EDTA, 10 $\mu$M phentolamine) maintained at 37° C., gassed with 95% $O_2$ and 5% $CO_2$, and maintained at an initial tension of 0.5 g, the resulting spontaneous locomotion was recorded. Each test compound was added cumulatively to the organ bath at intervals of 10 minutes, and the $EC_{50}$ value was calculated based on the area under the curve (AUC) for 10 minutes of spontaneous locomotion (Table 1).

TABLE 1

Spontaneous locomotion-suppressing effect on isolated rat colon

| Compound | (Example No.) | $EC_{50}$ (nM) |
|---|---|---|
| Compound 1 | (Example 15) | 1.4 |
| Compound 2 | (Example 11) | 3.7 |
| Compound 3 | (Example 45) | 3.3 |
| Compound 4 | (Example 43) | 3.8 |
| Compound 5 | (Example 32) | 12 |
| Compound 6 | (Example 28) | 15 |
| Compound 7 | (Example 60) | 42 |

TABLE 1-continued

Spontaneous locomotion-suppressing effect on isolated rat colon

| Compound | (Example No.) | $EC_{50}$ (nM) |
|---|---|---|
| Compound 8 | (Example 69) | 90 |
| SR 58611A | | 7.7 |

[Test 2] β3 adrenergic receptor stimulating effect

Isolated rat fat was used to examine the effect on fat decomposition. Fat was removed from around the testicles of rats (male SD rats), and shaken for 30 minutes in a nutrient medium (Krebs-Henseleit bicarbonate buffer, containing BSA, crude bacterial collagenase) maintained at 37° C., gassed with 95% $O_2$ and 5% $CO_2$. The shaken suspension was filtered with gauze, and the filtrate was centrifuged at 700 rpm for one minute, after which all but the upper adipocyte layer was suctioned out and discarded. More nutrient medium was added thereto, and washing was repeated 3 times. Finally, an appropriate amount of nutrient medium was added to make a suspension (adipocyte suspension preparation method).

A vehicle or test compound was added to the abovementioned suspension. Reaction was carried out by 30 minutes of shaking at 30° C. gassed with 95% $O_2$ and 5% $CO_2$. The reaction was terminated by addition of trichloroacetic acid, and after centrifugation at 3000 rpm for 15 minutes, the supernatant was collected. The pH was adjusted with a buffer solution, and then an oxidizing agent and coloring reagent were added, the OD value for 3-5-diacetyl-1,4-dihydrolutidine which hasmaximum absorption at 410 nm was measured, to assay the glycerol content generated. As a result, the lypolytic activity ($EC_{50}$ value) of test compound 1 (Embodiment 15) was 21 nM, compared to the activity ($EC_{50}$ value) for isoproterenol of 10 nM.

[Test 3] β2 adrenergic receptor stimulating effect

Isolated guinea pig tracheal muscle strips were used to examine the relaxing effect. The strips were isolated by removing guinea pig tracheal muscle by a common method. Each of the strips were mounted in an organ bath filled with a nutrient medium (Tyrode's buffer) maintained at 37° C., gassed with 95% $O_2$ and 5% $CO_2$, and then mounted under an initial tension of 1.0 g. Each test compound was added cumulatively to the organ bath at intervals of 10 minutes, and the change in relaxation of the tracheal muscle due to addition of the test compound was recorded with a recorder. The tracheal muscle-relaxing effect was represented as the molar concentration of the test compound at which 50% relaxation occurred with respect to maximum relaxation with isoproterenol ($EC_{50}$ value) (Table 2).

TABLE 2

Relaxing effect on isolated guinea pig tracheal muscle

| Compound | (Example No.) | $EC_{50}$ (nM) |
|---|---|---|
| Compound 1 | (Example 15) | 4,200 |
| Compound 2 | (Example 11) | 790 |
| Compound 3 | (Example 45) | 890 |
| Compound 4 | (Example 43) | 820 |
| Compound 5 | (Example 32) | 15,000 |
| Compound 6 | (Example 28) | 1,100 |
| Compound 7 | (Example 69) | 820 |
| SR 58611A | | 14,000 |

[Test 4] β1 adrenergic receptor stimulating effect

Isolated guinea pig right atrium strips were used to examine the heart beat increasing effect. Guinea pig right atriums were isolated by a common method, mounted in an organ bath filled with a nutrient medium (Krebs' buffer, 0.03 mM ascorbic acid, 0.03 mM EDTA, 10 M M phenanthramine) maintained at 37° C., gassed with 95% $O_2$ and 5% $CO_2$, and maintained at an initial tension of 0.5g, after which the cardiac contractile force and heart beats were recorded with a recorder. Each test compound was cumulatively added to the organ bath at intervals of 2.5 minutes, and the 10% augmentation value of the heart beats before and after administration ($EC_{10}$ value) was determined (Table 3).

TABLE 3

Heart beat increasing effect on isolated guinea pig right atrium

| Compound | (Example No.) | $EC_{10}$ (nM) |
|---|---|---|
| Compound 1 | (Example 15) | >30,000 |
| Compound 2 | (Example 11) | >30,000 |
| Compound 3 | (Example 45) | >30,000 |
| Compound 4 | (Example 43) | >30,000 |
| Compound 5 | (Example 32) | >30,000 |
| Compound 7 | (Example 69) | >30,000 |
| SR 58611A | | >30,000 |

[Test 5] Examination of relaxing effect on isolated rat bladder detrusor muscle (smooth muscle)

Rat bladders were isolated by a common method for preparation of strips. The isolated bladder strips were mounted in an organ bath filled with Krebs' solution kept at 37° C., under mixed gas aeration (95% $O_2$+5% $CO_2$) and subjected to an initial tension of 1.0 g. Each test compound was cumulatively added to the organ bath at intervals of 10 minutes. The activity of each test compound was represented as the relative relaxation rate, with 100% defined as the relaxation with addition of 1 μM isoproterenol, and the $EC_{50}$ value was calculated (Table 4).

TABLE 4

Relaxing effect on isolated rat bladder detrusor muscle

| Compound | (Example No.) | $EC_{50}$ (nM) |
|---|---|---|
| Compound 1 | (Example 15) | 16 |
| Clenbuterol | | 31 |
| Isoproterenol | | 10 |

[Test 6] Examination of suppressing effect on rat colon spontaneous locomotion (in vivo test)

The abdomens of urethane-anesthetized rats (male Wistar rats) were cut open and stitched (using suturing stitch with sterilized needle, 5-0, Nichiyo Kogyo) to a force transducer (F-081S, Star Medical) so as to allow recording of circular muscle contraction of the proximal colon (about 3 cm from the ileocecum) at the sternellum side. The lead wire of the force transducer was connected to a multipurpose preamp through a bridge box (FB-01, Star Medical), and the spontaneous locomotion of the colon was recorded with a Thermal Array Recorder (Nihon Koden), upon which the total degrees of contraction over 10 minutes were compared before and after bolus administration.

Each test compound was administered by polyethylene tube (0.05 ml/100 g b.w.) inserted into the femoral vein, and cumulative administration was carried out while confirming recovery of spontaneous locomotion. The spontaneous locomotion was recorded with a Magmate (Medical Research Equipment), and the $ED_{50}$ value was calculated based on the area under the curve for 10 minutes (Table 5).

TABLE 5

Suppressing effect on spontaneous locomotion of anesthetized rat colon (iv administration)

| Compound | (Example No.) | $ED_{50}$ (μg/kg, iv) |
|---|---|---|
| Compound 1 | (Example 15) | 0.27 |
| Compound 2 | (Example 11) | 0.23 |
| SR 58611A | | 12 |

[Test 7] Examination of suppressing effect on diarrhea using rat confinement stress-induced diarrhea models Each of the test compounds were orally administered to rats (male Wistar rats) which had been starved from 5:00 p.m. to 7:00 p.m. the previous day, and after one hour the rats were placed in a water immersed stress cage positioned vertically on an experiment stage, and the openings were capped for forced confinement. The nature of the feces excreted over a total of 3 hours was observed every 30 minutes, and the results were recorded as the diarrhea coefficient (0: no fecal excretion, 1: solid feces, 2: soft feces, 3: mild diarrhea, 4: muddy feces). Here, cases with a diarrhea coefficient score of 3 or higher, i.e. from feces which left a stain on filter paper to muddy feces, were judged as diarrhea, and the rate of diarrhea suppression was calculated (Table 6).

TABLE 6

Effect of diarrhea suppression in rat confinement stress-induced diarrhea models (diarrhea suppression rate %) po administration

| Compound | (Example No.) | Dose 1.0 mg/kg |
|---|---|---|
| Compound 1 | (Example 15) | 60 |
| Compound 2 | (Example 14) | 50 |
| Compound 3 | (Example 45) | 30 |
| Compound 4 | (Example 43) | 50 |
| SR 58611A | | 20 |

[Test 8] Examination of relaxing effect on anesthetized rat bladder

The abdomens of urethane-anesthetized rats (male Wistar rats) were cut open and small incisions were made in the top of bladder while avoiding the vessels for insertion, through a 3-way cock, of a pressure transducer, a balloon connected to a physiological saline injection syringe and a urine catheter, after which the incision was tied up with stitch, and the intravesical pressure was maintained at about 100 mm $H_2O$. Each test compound was administered through a polyethylene tube inserted into the femoral vein. The decrease of intravesical pressure after administration of each test compound was measured as an indicator of the effect of each test compound (FIG. 1).

[Test 9] Effect on bladder contraction induced by electrical stimulation of peripheral end of pelvic nerve in anesthetized rat After median incision in the abdomen of rats anesthetized with urethane and α-chloralose, the ureters on both sides were ligated and cut on the kidney side, and pledgets were placed on the cut sections to absorb the urine. Next, the hypogastric nerves on both sides were transected and the base of the penis were ligated at close the urethra. A small hole was opened in the top of bladder and, after inserting one end of a polyethylene tube, ligated. The other end of the polyethylene tube was connected to a pressure transducer (TP 400, Nihon Koden) to measure the intravesical pressure.

Physiological saline was injected into the bladder to obtain intravesical pressure at a 100 mm $H_2O$. The change of the intervesical pressure was recorded with a heat recorder (WT 685G, Nihon Koden). After ablating the left pelvic nerves from the fatty tissue around the bladder and cutting the central section, a platinum electrode was implanted at the peripheral end of the pelvic nerves. An electrical stimulation apparatus (SEN-3301, Nihon Koden) was used for generating a rectangular wave electrical stimulation (20 Hz, 0.3 msec, 5V) for 5 seconds every 5 minutes. During the experiment, the abdomen was filled with liquid paraffin kept at 37° C. to prevent drying of the nerves and organs.

After confirming a nearly consistent reaction by the electrical stimulation, physiological saline (0.05 ml/100 g rat weight) was administered over a period of about one minute through the polyethylene tube inserted in the femoral vein, and then after 20 minutes the test compounds were administered.

Figure 2:
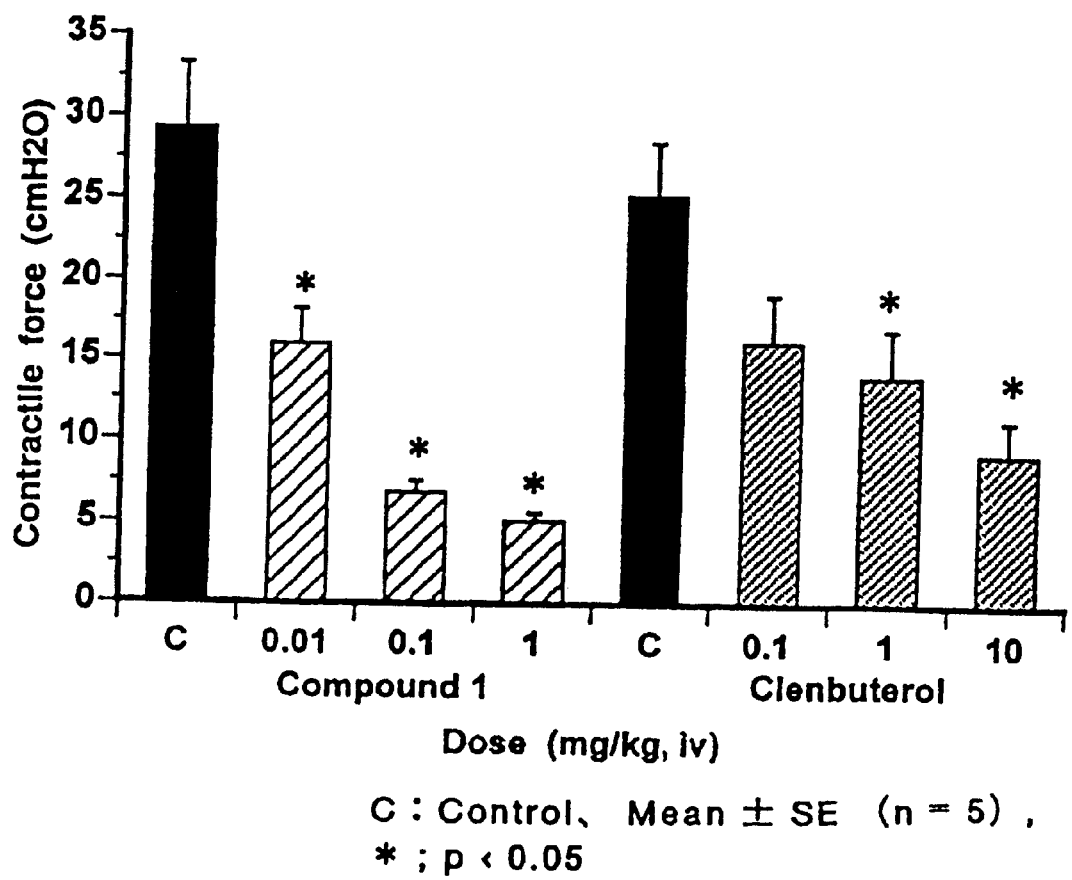
FIG. 2 is an illustration of the contraction-suppressing effect of test compounds against bladder contraction caused by peripheral electrical stimulation of anesthetized rat pelvic plexus.

As a result, compound 1 suppressed bladder contraction at a lower dose than Clenbuterol hydrochloride (FIG. 2).

As these experimental results clearly demonstrate, the compounds of the invention have a strong β3 adrenergic receptor-stimulating action, and selectivity for β3 adrenergic receptor was high.

No particularly serious toxicity was found even with oral administration of 1000 mg/kg of the compounds of the invention to male rats (300–350 g body weight), showing the compounds to be highly safe.

The compounds of the invention are normally to be administered in the form of pharmaceutical preparations in admixture with pharmaceutical carriers. Pharmaceutical carriers are commonly used in the field of medicinal preparations, and substances which do not react with the compounds of the invention should be used.

As examples there may be mentioned lactose, glucose, mannit, dextrin, starch, white sugar, magnesium aluminate metasilicate, synthetic aluminum silicate, crystalline cellulose, carboxymethyl cellulose calcium, microcrystalline cellulose, dry corn starch, methyl cellulose, gum Arabic, gelatin, hydroxypropyl cellulose, hydroxypropylmethyl cellulose, polyvinyl pyrrolidone, polyvinyl alcohol, magnesium stearate, talc, carboxyvinyl polymer, titanium oxide, sodium lauryl sulfate, glycerin, fatty acid glycerin esters, purified lanolin, polysorbate, macrogol, vegetable oil, wax, non-ionic surfactants, propylene glycol and water, etc.

The preparation may be in the form of tablets, capsules, granules, powder, syrup, suspension, suppository, gel, injection or the like. These pharmaceutical preparations may be prepared by conventional methods.

The preparations may contain the compounds of the invention in a proportion of 0.01% or greater, and preferably from 0.1 to 50%. They may also contain other therapeutically effective components.

When a compound of the invention or its pharmacologically acceptable salt is used as a β3 adrenergic receptor agonist it may be administered either orally or parenterally, but oral administration is preferred. The dosage will differ depending on the mode of administration, the symptoms and age of the patient and the kind of procedural measure (therapy or prevention), but administration will normally be 0.01 to 1000 mg/individual, preferably 0.1 to 100 mg/individual, and more preferably 0.1 to 50 mg/individual, given from 1 to 4 times per day.

Reference examples and examples of production processes for compounds of the present invention will now be explained, with the understanding that the invention is in no way limited to these examples. The structures of the compounds were determined by 1H-NMR or MS spectrometry.

REFERENCE EXAMPLE 1

3-Iodoanisole (75g), 2-cyclohexen-1-ol (15g), potassium bicarbonate (45 g), tetrabutylammonium chloride (45 g) and palladium acetate (1.8 g) were heated and stirred for 80 hours at an external temperature of 60° C. and under an argon air flow, using acetonitrile (300 ml) as the solvent. After concentrating the reaction solution under reduced pressure, an aqueous ammonium chloride solution was added and extraction was performed with diethyl ether. After washing the organic layer with saturated saline, it was dried with anhydrous magnesium sulfate. The crude product obtained from distilling off the solvent under reduced pressure was separated and purified by silica gel chromatography (n-hexane:ethyl acetate=20:1) to give 6.1 g of 3-(3-methoxyphenyl) cyclohexanone (19.6% yield).

1H-NMR(CDCl$_3$) δ ppm:1.65–2.18(4H,m), 2.25–2.61 (4H,m), 2.90–3.00(1H,m), 3.79(3H,s), 6.76–6.82(3H,m), 7.20–7.26(1H,m).

REFERENCE EXAMPLE 2

3-(3-Methoxyphenyl)cyclohexanone (13.1 g), benzylamine (6.88 g) and p-toluenesulfonic acid (1.22 g) were refluxed for 1.5 hours in benzene (200 ml) using a Dean-Stark apparatus while removing the water generated. After concentrating the reaction solution under reduced pressure, methanol (200 ml) was added and upon adding sodium borohydride (2.43 g) gradually under ice cooling, the mixture was stirred at room temperature for an hour. After concentrating the reaction solution under reduced pressure, water was added and extraction was performed with chloroform. The organic layer was washed with saturated aqueous solution of sodium bicarbonate and saturated saline, and then dried with anhydrous magnesium sulfate. The crude product obtained from distilling off the solvent under reduced pressure was separated and purified by silica gel column chromatography (n-hexane:ethyl acetate=5:1 to 1:1) to give 15.8 g of N-benzyl-N-[3-(3-methoxyphenyl) cyclohexyl]amine as a diastereomeric mixture (83.4% yield). Repeated silica gel column chromatography (n-hexane:ethyl acetate=5:1) allowed separation of the two diastereomers, with the trans form obtained from the earlier eluted fraction and the cis form obtained from the later eluted fraction.

trans form(R*R*)1H-NMR(CDCl$_3$) δ ppm:1.40–2.00 (9H,m), 2.90–3.09(2H,m), 3.80(3H,s), 3.81(2H,s), 6.68–6.83(3H,m), 7.20–7.40 (6H,m).

cis form(R*S*)1H-NMR(CDCl$_3$) δ ppm:1.06–1.58(5H, m), 1.76–2.20(4H,m), 2.45–2.72(2H,m), 3.78(3H,s), 3.80 (2H,s), 6.68– 6.85(3H,m), 7.15–7.35(5H,m).

REFERENCE EXAMPLE 3

(trans)-N-Benzyl-N-[3-(3-methoxyphenyl)cyclohexyl] amine (6.59 g) was dissolved in ethyl acetate (20 ml), and then 4 N HCl-ethyl acetate solution (20 ml) was added while cooling on ice, and the mixture was stirred at room temperature for 30 minutes. After concentrating the reaction solution under reduced pressure, 10% palladium-carbon (1.3 g) and acetic acid (60 ml) were added for hydrogen addition at an external temperature of 80° C. for 8 hours. After filtering off the solvent from the reaction solution, the solvent was concentrated under reduced pressure (repeated azeotropy with ethanol and toluene) to give 5.40 g of (trans)-3-(3-methoxyphenyl)cyclohexylamine hydrochloride (quantitative yield).

1H-NMR(CDCl$_3$) δ ppm: (free compound) 1.40–1.93 (10H,m), 2.84–3.00(1H,m), 3.30–3.35(1H,m), 3.80(3H,s), 6.68–6.85(3H,m), 7.16–7.26(1H,m).

Debenzylation of the cis form by the same method gave (cis)-3-(3-methoxyphenyl) cyclohexylamine hydrochloride.

1H-NMR(CD$_3$OD) δ ppm:1.34–1.65(4H,m), 1.82–2.22 (4H,m), 2.60–2.72(1H,m), 3.17–3.30(1H,m), 3.78(3H,s), 6.71–6.85 (3H,m), 7.19–7.25(1H,m)

The following compounds were synthesized according to the method of Reference Examples 1 to 3.

REFERENCE EXAMPLE 4

3-(4-Methoxyphenyl)cyclohexanone

1H-NMR(CDCl$_3$) δ ppm:1.76–1.84(2H,m), 2.03–2.15 (2H,m), 2.35–2.57(4H,m), 2.90–3.03(1H,m), 3.80(3H,s), 6.87(2H,d, J=6.71 Hz), 7.14(2H,d, J=6.71 Hz).

REFERENCE EXAMPLE 5

(trans)-N-Benzyl-N-[3-(4-methoxyphenyl)cyclohexyl] amine hydrochloride

1H-NMR(CDCl$_3$) δ ppm:1.25–2.30(8H,m), 3.19(1H, broad s), 3.35(1H,m), 3.75(3H,s), 4.12(2H,broad s), 6.75 (2H,d, J=8.55 Hz), 7.13(2H,d, J=8.55 Hz), 7.33–7.38(3H, m), 7.66–7.69 (2H,m), 9.92(2H,broad s).

(cis)-N-Benzyl-N-[3-(4-methoxyphenyl) cyclohexyl] amine hydrochloride

1H-NMR(CDCl$_3$) δ ppm:1.19–1.27(2H,m), 1.58–1.94 (4H,m), 2.19–2.42(3H,m), 2.88(1H,broad s), 3.75(3H,s), 3.98(2H,broad s), 6.78(2H,d, J=8.55 Hz), 7.08(2H,d, J=8.55 Hz), 7.35–7.38(3H,m), 7.61–7.64(2H,m), 9.88(2H,broad s).

REFERENCE EXAMPLE 6

(trans)-3-(4-methoxyphenyl) cyclohexylamine hydrochloride

1H-NMR(CDCl$_3$+CD$_3$OD) δ ppm:1.53–2.16(8H,m), 2.88–3.00, (1H,m), 3.53–3.62(1H,m), 3.80(3H,s), 6.86(2H, d, J=8.55 Hz), 7.17(2H,d, J=8.55 Hz).

(cis)-3-(4-Methoxyphenyl)cyclohexylamine hydrochloride 1H-NMR(CDCl$_3$+CD$_3$OD) δ ppm:1.34–1.61(4H,m), 1.84–2.04(2H,m), 2.09–2.26(2H,m), 2.53–2.65(1H,m), 3.12–3.25(1H,m), 3.80(3H,s), 6.85(2H,d, J=8.55 Hz), 7.13 (2H,d, J=8.55 Hz).

REFERENCE EXAMPLE 7

3-(2-Methoxyphenyl)cyclohexanone

1H-NMR(CDCl$_3$) δ ppm:1.70–2.00(2H,m), 2.00–2.22 (2H,m), 2.25–2.63(4H,m), 3.30–3.49(1H,m), 3.82(3H,s), 6.80–7.00(2H,m), 7.15–7.24 (2H,m)

REFERENCE EXAMPLE 8

(trans)-3-(2-Methoxyphenyl) cyclohexylamine hydrochloride

1H-NMR(CDCl$_3$) δ ppm:1.50–2.32(8H,m), 3.40–3.55 (1H,m), 3.71–3.80(1H,m), 3.73(3H,s), 6.71–6.90(2H,m), 7.10–7.20 (2H,m).

(cis)-3-(2-Methoxyphenyl)cyclohexylamine hydrochloride

1H-NMR(CDCl$_3$) δ ppm:1.35–2.00(6H,m), 2.20–2.30 (2H,m), 2.91–3.10(1H,m), 3.22–3.35(1H,m), 3.79(3H,s), 6.80–6.92(2H,m), 7.13–7.20(2H,m).

REFERENCE EXAMPLE 9

3,4-Dimethoxybenzaldehyde (30.1 g) was dissolved in acetone (900 ml), and then piperidine (23.2 ml) and acetic acid (13.4 ml) were added prior to reflux for 4 hours. After distilling off the reaction solvent under reduced pressure, it was dissolved in 600 ml of ethyl acetate and washed with saturated sodium bicarbonate water and saturated saline. After drying with anhydrous magnesium sulfate, the solvent was distilled off under reduced pressure producing yellow crystals which were then washed in isopropyl ether to give 21.0 g of 4-(3,4-dimethoxyphenyl)-3-buten-2-one (56.4%).

1H-NMR(CDCl$_3$) δ ppm:2.38(3H,s), 3.92(6H,s), 6.61 (1H,d, J=15.9 Hz), 6.88(1H,d, J=7.94 Hz), 7.08(1H,s), 7.13 (1H,d, J=7.94 Hz), 7.47(1H,d, J=15.9 Hz).

REFERENCE EXAMPLE 10

Diethyl malonate (73. 7 g) was dissolved in ethanol (700 ml), and then potassium tert-butoxide (51.6 g) was gradually added thereto. A solution of 4-(3,4-dimethoxyphenyl)-3-buten-2-one (79.1 g) in ethanol (500 ml) was added dropwise, and the mixture was refluxed for 1.5 hours. After distilling off the reaction solvent under reduced pressure, ice water was poured over it and it was adjusted to pH4 with concentrated hydrochloric acid. The deposited crystals were filtered by suction, washed with water and then air-dried to give 122 g of ethyl 2-(3,4-dimethoxyphenyl)-4,6-dioxocyclohexane carboxylate (99.6%).

1H-NMR(CDCl$_3$) δ ppm:1.05–1.25(3H,m), 2.40–2.98 (3H,m), 3.44–3.65(2H,m), 3.86(6H,s), 4.04–4.31(2H,m), 6.71–6.84(2H,m), 7.26(1H,s).

REFERENCE EXAMPLE 11

10% Aqueous solution of potassium hydroxide (760 ml) was added to ethyl 2-(3,4-dimethoxyphenyl)-4,6-dioxocyclohexane carboxylate (122 g), and the mixture was refluxed for 3.5 hours. After cooling the reaction solution on ice, it was adjusted to pH1 with concentrated hydrochloric acid, and stirred at 50° C. for an hour. After allowing the reaction solution to cool, the deposited crystals were filtered by suction and washed with purified water and isopropyl ether to give 85.8 g of 5-(3,4-dimethoxyphenyl) cyclohexane-1,3-dione (90.5%).

1H-NMR(DMSO-d$_6$) δ ppm:2.40–2.77(4H,m), 3.59–3.63 (2H,m), 3.75(3H,s), 3.76(3H,s), 5.36(1H,s), 6.84(2H,s), 6.97(1H,s).

REFERENCE EXAMPLE 12

5-(3,4-Dimethoxyphenyl)cyclohexan-1,3-dione (31.8 g) was suspended in ethanol (500 ml), and concentrated hydrochloric acid (20 ml) was added prior to reflux for 3 hours. After the reaction solvent was concentrated under reduced pressure, it was dissolved in chloroform and washed with saturated sodium bicarbonate water. After drying with anhydrous magnesium sulfate, the solvent was concentrated under reduced pressure producing crude crystals which were then washed with diethyl ether to give 10.3 g of 5-(3,4-dimethoxyphenyl)-3-ethoxy-2-cyclohexen-1-one (29.1%).

1H-NMR(CDCl$_3$) δ ppm:1.38(3H,t, J=7.32 Hz), 2.48–2.70(4H,m), 3.26–3.38(1H,m), 3.87–3.99(8H,m), 5.43 (1H,s), 6.76–6.86(3H,m).

REFERENCE EXAMPLE 13

5-(3,4-Dimethoxyphenyl)-3-ethoxy-2-cyclohexen-1-one (16.7 g) was dissolved in ethanol (260 ml), and then sodium borohydride (6.88 g) was gradually added and the mixture was stirred at 60° C. for 1.5 hours. After distilling off the reaction solvent under reduced pressure, and subsequent pouring over of ice water, extraction with ethyl acetate and drying with anhydrous magnesium sulfate, the solvent was concentrated under reduced pressure to produce a yellow oily substance. The oily substance was dissolved in ethyl acetate (20 ml), 4 N HCl-ethyl acetate solution (50 ml) was added and the mixture was stirred at room temperature for 13 hours. The reaction solution was washed with saturated sodium bicarbonate water and saturated saline and dried with anhydrous magnesium sulfate, after which the solvent was distilled off under reduced pressure to produce a yellow oily substance which was then purified by silica gel column chromatography (n-hexane:ethyl acetate=2:1). The resulting crystals were washed with diethyl ether to give 6.76 g of 5-(3,4-dimethoxyphenyl)-2-cyclohexen-1-one (48.1%).

1H-NMR(CDCl$_3$) δ ppm:2.46–2.76(4H,m), 3.24–3.37 (1H,m), 3.87(3H,s), 3.88(3H,s), 6.13(1H,d, J=10.4 Hz), 6.76–6.87(3H,m), 7.02–7.09(1H,m).

REFERENCE EXAMPLE 14

5-(3,4-Dimethoxyphenyl)-2-cyclohexen-1-one (6.76 g) was dissolved in ethanol (100 ml), and 10% palladium-carbon (684 mg) was added thereto. After substituting the reaction vessel with hydrogen gas, hydrogen addition was effected for 30 minutes at normal pressure and room temperature. After the reaction, the catalyst was filtered off and the solvent was distilled off under reduced pressure to produce an oily substance which was dissolved in ethyl acetate (50 ml), and then 4 N HCl-ethyl acetate solution (2 ml) was added and the mixture was stirred at room temperature for 20 minutes. The solvent was distilled off under reduced pressure to produce crude crystals which were then washed with n-hexane to give 6.72 g of 3-(3,4-dimethoxyphenyl)cyclohexanone (98.5%).

1H-NMR(CDCl$_3$) δ ppm:1.74–1.91(2H,m), 2.07–2.16 (2H,m), 2.37–2.62(4H,m), 2.91–3.03(1H,m), 3.87(3H,s), 3.89(3H,s), 6.74–6.85(3H,m)

REFERENCE EXAMPLE 15

3-(3,4-Dimethoxyphenyl)cyclohexanone (6.90 g) and benzylamine (3.16 g) were refluxed for 1.5 hours in benzene (150 ml) in the presence of para-toluenesulfonic acid (630 mg), using a Dean-Stark apparatus while removing the water generated. After distilling off the benzene under reduced pressure, it was dissolved in methanol (120 ml) while cooling on ice, sodium borohydride (1.12 g) was gradually added and the mixture was stirred at room temperature for an hour. After concentrating the reaction solution, water was added, extraction was performed with chloroform, and the solution was washed with saturated sodium bicarbonate water and saturated saline. After drying with anhydrous magnesium sulfate, the solvent was distilled off under reduced pressure to produce a light yellow oily substance which was then separated and purified by silica gel column chromatography (n-hexane:ethyl acetate=5:1→1:1→1:2), to give 3.16 g of (trans)-N-benzyl-N-[3-(3,4-dimethoxyphenyl) cyclohexyl]amine (33.2% yield) and 3.09 g of (cis)-N-benzyl-N-[3-(3,4-dimethoxyphenyl) cyclohexyl]amine (32.4% yield).

1H-NMR(CDCl$_3$) δ ppm: (trans)1.43–1.95(9H,m), 2.89–2.98, (1H,m), 3.07 (1H,brs) ,3.80 (2H, s), 3.84 (3H, s), 3.86 (3H, s), 6.73–6.81(3H,m), 7.24–7.37(5H,m). 1H-NMR (CDCl$_3$) δ ppm: (cis)1.14–1.53(5H,m), 1.80–2.18(4H,m), 2.47–2.55(1H,m), 2.55–2.70(1H,m), 3.84(2H,s), 3.86(3H,s), 3.87(3H,s), 6.74–6.83 (3H,m), 7.24–7.33(5H,m).

REFERENCE EXAMPLE 16

N-Benzyl-N-[3-(3,4-dimethoxyphenyl)cyclohexyl]amine (3.16 g) was dissolved in ethyl acetate, 4 N HCl-ethyl acetate solution was added, and the mixture was stirred at room temperature for 30 minutes. After concentrating the solvent under reduced pressure, it was dissolved in acetic acid (100 ml), and 10% palladium-carbon (640 mg) was added thereto. After substituting the reaction vessel with hydrogen gas, hydrogen addition was effected for 3 hours at normal pressure, at 80° C. After the reaction, the catalyst was filtered off and the solvent was distilled off under reduced pressure to produce crude crystals which were then washed with diethyl ether to give 2.80 g of 3-(3,4-dimethoxyphenyl)cyclohexylamine hydrochloride (quantitative yield).

1H-NMR(CDCl$_3$) δ ppm: (trans)1.48–2.28(8H,m), 3.13–3.20 (1H,m), 3.71–3.93(7H,m), 6.69–6.79(3H,m). 1H-NMR(CD$_3$OD) δ ppm: (cis)1.39–1.59(4H,m), 1.87–2.17(4H,m), 2.59–2.68(1H,m), 3.18–3.32(1H,m), 3.82 (3H,m), 3.84(3H,s), 6.77–6.90(3H,m).

REFERENCE EXAMPLE 17

Grignard reagent was prepared from magnesium (2.8 g) and 3-bromoanisole (22.0 g) in tetrahydrofuran (50 ml) in the presence of iodine, and a catalytic amount of copper (I) bromide (CuBr, 0.83 g) was added thereto. A tetrahydrofuran (10 ml) solution containing 2-cyclohexen-1-one (9.6 g) was also added dropwise while stirring on ice. After stirring at room temperature for 3 hours, hydrochloric acid was added, and extraction was performed with ethyl acetate. After drying with anhydrous magnesium sulfate, the solvent was distilled off under reduced pressure to produce a light yellow oily substance which was then separated and purified by silica gel column chromatography (n-hexane:ethyl acetate=5:1) to give 9.7 g of 3-(3-methoxyphenyl) cyclohexanone (47.6% yield).

REFERENCE EXAMPLE 18

Raney nickel (0.5 g) was added to a solution of 3-(3-methoxyphenyl)cyclohexanone (2.05 g) and (S)-1-phenylethylamine (1.22 g) in ethanol (20 ml) prior to room temperature stirring and hydrogen addition. After the starting materials were consumed, the catalyst was filtered off, and the filtrate was distilled off under reduced pressure to produce a light yellow oily substance which was then separated and purified by silica gel column chromatography (chloroform:methanol=50:1) to give 1.62 g of N-[3-(3-methoxyphenyl) cyclohexyl]-N-(1-phenylethyl)amine (a mixture of trans-H form and trans-L form) (52.5% yield). The proportion of trans form to cis form with this reaction was about 12 to 1 (confirmed by HPLC) . Repeated column chromatography enabled separation of trans-H and trans-L.

(Trans-H) Synthesis material for compound of Example 11 (optically active compound)

1H-NMR(CDCl$_3$) δ ppm:1.34–1.87(11H,m), 2.82–2.90 (2H,m), 3.77 (3H,s), 3.82–3.90(1H,m), 6.73–6.83(3H,m), 7.13–7.37(6H,m).

(Trans-L) synthesis material for compound of Example 12 (optically active compound)

1H-NMR(CD$_3$OD) δ ppm:1.36–1.97(11H,m), 2.87–2.92 (2H,m), 3.80 (3H,s), 3.84–3.91(1H,m), 6.71–6.83(3H,m), 7.18–7.32(6H,m).

REFERENCE EXAMPLE 19

The compound of Reference Example 18 (mixture of trans-H and trans-L) was subjected to hydrogen addition in ethanol in the presence of 10% palladium-carbon while heating at 50° C., to give 3-(3-methoxyphenyl) cyclohexylamine (a mixture of trans-H and trans-L). Reduction reaction from trans-H and trans-L in the same manner gave optically active 3-(3-methoxyphenyl) cyclohexylamine.

(Optical resolution)

3-(3-Methoxyphenyl) cyclohexylamine (a mixture of trans-H and trans-L) (35.7 g) was dissolved in ethanol (20 ml), a solution of (S)-mandelic acid (26.5 g) in ethanol (50 ml) was added, and the mixture was stirred for 30 minutes on ice. The deposited crystals were filtered by suction and air-dried to give 24.0 g of 3-(3-methoxyphenyl) cyclohexylamine.(S)-mandelate (yield: 38.6%, 78.5% ee) (crystal 1). Crystal 1 was suspended in ethanol (48 ml), refluxed for 30 minutes and allowed to cool to room temperature, and then stirred while cooling on ice. The crystals were filtered by suction and air-dried to give 19.1 g of salt (yield: 79.6%, 98.0% ee) (crystal 2). The same procedure was carried out once more to give 18.4 g of salt (yield: 96.0%, 99.6% ee) (crystal 3). The optical purity of crystal 1 and 2 was measured by HPLC after preparing free compounds. For crystal 3, it was measured by HPLC upon acetylation of the primary amino group, by the method described in the next reference example. After adding water (150 ml) to crystal 3 and rendering them alkaline with concentrated ammonia water, extraction was performed with ethyl acetate. After washing with saturated sodium bicarbonate water and saturated saline and drying with anhydrous magnesium sulfate, the solvent was distilled off under reduced pressure to give 14.0 g of optically active (trans)-3-(3-methoxyphenyl)cyclohexylamine (quantitative yield)

1H-NMR(CDCl$_3$) δ ppm:1.42–2.04(10H,m), 2.90–3.01 (1H,m), 3.38(1H,br s), 3.79(3H,s), 6.71–6.84(3H,m), 7.16–7.23(1H,m).

(hydrochloride)mp.123.5–125.0° C., $[\alpha]_D$=−13.9° (c=1.00,CHCl$_3$) MS(m/z):206(M+1). ((S)-mandelate) mp.181.0–182.5° C., $[\alpha]_D$=+32.6° (c=1.00, CH$_3$OH).

REFERENCE EXAMPLE 20

Acetic anhydride (1 ml) and pyridine (0.5 ml) were added to (trans)-3-(3-methoxyphenyl) cyclohexylamine (10 mg) and the mixture was stirred at 50° C. for 2 hours. The reaction solution was poured into glacial sodium bicarbonate water and extracted with ethyl acetate. The organic layer was washed with 1 N hydrochloric acid, saturated sodium bicarbonate water and saturated saline and dried with anhydrous magnesium sulfate, and then the solvent was distilled off under reduced pressure to give 8 mg of N-acetyl-N-[3-(3-methoxyphenyl)cyclohexyl]amine (53.3%).

1H-NMR(CDCl$_3$) δ ppm:1.25–1.99(8H,m), 2.03(3H,s), 2.55–2.70 (1H,m), 3.80(3H,s), 4.28–4.32(1H,m), 5.76(1H, br s), 6.72–6.82 (3H,m), 7.19–7.25(1H,m).

REFERENCE EXAMPLE 21

47% Hydrobromic acid (140 ml) was gradually added to (trans)-3-(3-methoxyphenyl) cyclohexylamine (14.0 g) and the mixture was refluxed for an hour. After adjusting the reaction solution to pH7 with sodium bicarbonate (powder), it was adjusted to pH9 with concentrated ammonia water. After filtering the deposited crystals by suction and washing with water, they were dried by ventilation at 45° C. for 5 hours to give 8.58 g of (trans)-3-(3-aminocyclohexyl)phenol (65.8% yield).

1H-NMR(CD$_3$OD) δ ppm:1.49–1.84(8H,m), 2.79–2.87 (pH,m), 3.23(1H,br s), 6.58(1H,dd, J=1.22, 7.93 Hz), 6.67–6.68(2H,m), 7.07(1H,t, J=7.93 Hz).

REFERENCE EXAMPLE 22

(trans)-3-(3-Aminocyclohexyl)phenol (7.39 g) was dissolved in DMF (50 ml), and after adding a solution of di-tert-butylcarbonate (8.43 g) in DMF (20 ml) and triethylamine (11.7 g), the mixture was stirred at room temperature for 2 hours. Ethyl acetate was added to the reaction solution, and after washing 3 times with water and once with saturated saline, it was dried with anhydrous magnesium sulfate. The solvent was distilled off under reduced pressure to produce a crude product which was then separated and purified by silica gel column chromatography (n-hexane:ethyl acetate= 3:1) to give 10.1 g of (trans)-3-[3-(N-tert-butoxycarbonylaminocyclohexyl)]phenol (89.5% yield).

1H-NMR(CDCl$_3$) δ ppm:1.47–1.96(17H,m), 2.63–2.71 (1H,m), 3.99(1H,br s), 4.81(1H,br s), 6.65–6.78(3H,m), 7.15 (1H,t, J=7.32 Hz).

REFERENCE EXAMPLE 23

(trans)-3-[3-(N-tert-Butoxycarbonylaminocyclohexyl)] phenol (10.1 g) was dissolved in acetone (50 ml), and upon adding potassium carbonate (9.55 g) and ethyl bromoacetate (5.76 g) the mixture was refluxed for 3.5 hours. After the reaction, the precipitated salt was filtered off and the solvent was distilled off under reduced pressure. The resulting crude product was separated and purified by silica gel column chromatography (n-hexane:ethyl acetate=3:1) to give 12.8 g of ethyl[3-[3-(N-tert-butoxycarbonylaminocyclohexyl) phenoxy]]acetate (98.4% yield).

1H-NMR(CDCl$_3$) δ ppm:1.30(3H,t, J=7.32 Hz), 1.46–1.99(17H,m), 2.55–2.70(1H,m), 4.00(1H,br s), 4.27 (2H,q, J=7.32 Hz), 4.61(2H,s), 4.80(1H,br s), 6.71(1H,dd, J=2.44, 7.94 Hz), 6.73–6.86(2H,m), 7.21(1H,t, J=7.94 Hz).

REFERENCE EXAMPLE 24

Ethyl [3-[3-(N-tert-butoxycarbonylaminocyclohexyl) phenoxy]]acetate (12.8 g) was dissolved in ethyl acetate (15 ml), and upon adding 4 N HCl-ethyl acetate solution (25 ml) the mixture was stirred for 25 hours at room temperature. After adding water to the reaction solution, it was rendered weakly alkaline with concentrated ammonia water and extraction was performed with ethyl acetate. After washing the organic layer with saturated sodium bicarbonate water and saturated saline, it was dried with anhydrous magnesium sulfate and the solvent was distilled off under reduced pressure to give 8.47 g of ethyl 3-(3-aminocyclohexyl) phenoxyacetate as an oily substance (89.7% yield)

1H-NMR(CDCl$_3$) δ ppm:1.30(3H,t, J=7.32 Hz), 1.44–1.87(8H,m), 2.15(2H,br s), 2.94–2.98(1H,m), 3.36–3.39(1H,m), 4.27(2H,q, J=7.32 Hz), 4.60(2H,s), 6.70 (1H,dd, J=2.44, 7.94 Hz), 6.82–6.88(2H,m), 7.20(1H,t, J=7.94 Hz). $[\alpha]_D$=−1°. (c=1.09,MeOH).

(fumaric acid salt) mp. 148.0–149.5° C., $[\alpha]_D$=−10.3°(c= 1.00, MeOH). Elemental analysis: (as $C_{20}H_{27}NO_7$) Calculated: C; 61.06, H; 6.92, N; 3.56 Found: C; 60.93, H; 6.93, N; 3.40

REFERENCE EXAMPLE 25

After adding potassium tert-butoxide to a solution of ethyl acetoacetate (25.7 g) in benzene (420 ml) while cooling on ice, 4-methoxyphenacyl bromide (24.8 g) was gradually added and the mixture was refluxed for an hour. After allowing the reaction solution to cool, it was washed with 5% sodium hydroxide and purified water, and dried with anhydrous magnesium sulfate. The solvent was distilled off under reduced pressure to give 26.2 g of ethyl 2-[2-(4-methoxyphenyl)-2-oxoethyl]-4-oxopentanoate (87.0% yield).

1H-NMR(CDCl$_3$) δ ppm:1.29(3H,t, J=7.32 Hz), 2.44(3H, s), 3.47(1H,dd, J=5.49, 18.3 Hz), 3.67(1H,dd, J=8.54, 18.3 Hz), 3.87 (3H,s), 4.22(3H,m), 6.93(2H,d, J=8.55 Hz), 7.96 (2H,d, J=8.55 Hz).

REFERENCE EXAMPLE 26

To ethyl 2-[2-(4-methoxyphenyl)-2-oxoethyl]-4-oxopentanoate (26.2 g) there was added 1000 ml of 1% aqueous potassium hydroxide solution, and the mixture was refluxed for an hour. Next, potassium hydroxide was added so that the aqueous potassium hydroxide solution reached a concentration of 10% (adding a solution of 146 g of potassium hydroxide in 200 ml of water), and the mixture was further refluxed for 2 hours. After allowing the reaction solution to cool, extraction was performed with ethyl acetate and water washing was then followed by drying with anhydrous magnesium sulfate. The solvent was distilled off under reduced pressure to produce crude crystals which were then washed with diethyl ether to give 11.4 g of 3-(4-methoxyphenyl)-2-cyclopenten-1-one (64.4% yield).

1H-NMR(CDCl$_3$) δ ppm:2.56–2.59(2H,m), 3.01–3.04 (2H,m), 3.87 (3H,s), 6.48(1H,s), 6.96(2H,d, J=8.55 Hz), 7.63(2H,d, J=8.55 Hz).

REFERENCE EXAMPLE 27

3-(4-Methoxyphenyl)-2-cyclopenten-1-one (11.2 g) was dissolved in ethanol, and 10% palladium-carbon (1.1 g) was added thereto. After substituting the reaction vessel with hydrogen gas, hydrogen addition was carried out at normal pressure, 40° C. for 4 hours. After the reaction, the catalyst was filtered off and the solvent was distilled off under reduced pressure to produce a light yellow oily substance which was then purified by silica gel column chromatography (n-hexane:ethyl acetate=5:1) to give 5.90 g of 3-(4-methoxyphenyl) cyclopentanone (52.2% yield).

1H-NMR(CDCl$_3$) δ ppm:1.91–2.03(1H,m), 2.24–2.51 (4H,m), 2.65(1H,dd, J=7.32, 17.7 Hz), 3.34–3.40(1H,m), 3.80(3H,s), 6.88(2H,d, J=8.55 Hz), 7.18(2H,d, J=8.55 Hz).

REFERENCE EXAMPLE 28

3-(4-Methoxyphenyl) cyclopentanone (7.37 g) and benzylamine (4.15 g) were refluxed for 1.25 hours in benzene (150 ml) in the presence of p-toluenesulfonic acid (820 mg) using a Dean-Stark apparatus while removing the water generated. After distilling off the benzene under reduced pressure, it was dissolved in methanol (150 ml) while cooling on ice, sodium borohydride (1.63 g) was gradually added and the mixture was stirred at room temperature for 12.5 hours. After concentrating the reaction solution, water was added, and extraction with chloroform was followed by washing with saturated sodium bicarbonate water and saturated saline. After drying with anhydrous magnesium sulfate, the solvent was distilled off under reduced pressure to produce a light yellow oily substance which was then purified by silica gel column chromatography (n-hexane:ethyl acetate=2:1) to give 10.0 g of N-benzyl-N-[3-(4-methoxyphenyl)cyclopentyl]amine (91.7% yield).

1H-NMR(CDCl$_3$) δ ppm:1.51–2.43(6H,m), 3.00–3.20 (1H,m), 3.37–3.47 (1H,m), 3.84–3.89(5H,m), 6.94(2H,d, J=7.94 Hz), 7.24–7.44(7H,m).

REFERENCE EXAMPLE 29

N-Benzyl-N-[3-(4-methoxyphenyl)cyclopentyl]amine (10.0 g) was dissolved in ethanol (120 ml), 55 ml of 1 N hydrochloric acid was added, and the mixture was stirred at 40° C. for 3 hours. The crystals (hydrochloride) obtained by concentrating the reaction solution were dissolved in acetic acid (130 ml), and 10% palladium-carbon (1.3 g) was added. After substituting the reaction vessel with hydrogen gas, hydrogen addition was carried out at normal pressure, 80° C. for 5 hours. After the reaction, the catalyst was filtered off and the solvent was distilled off under reduced pressure to produce light yellow crystals which were then washed with diethyl ether to give 4.55 g of 3-(4-methoxyphenyl) cyclopentylamine hydrochloride (99.8%).

1H-NMR(CDCl$_3$) δ ppm:(a mixture of cis and trans) 1.59–1.62 (1H,m), 1.81–2.26(10H,m), 2.50–2.55(1H,m), 2.85–3.05(1H,m), 3.30–3.50(1H,m), 3.70–3.80(8H,m), 6.75 (4H,d, J=7.94 Hz), 7.05(2H,d, J=7.94 Hz), 7.15(2H,d, J=7.94 Hz).

REFERENCE EXAMPLE 30

3-(4-Methoxyphenyl)cyclopentanone (8.51 g) and methoxymethyltriphenylphosphonium chloride (16.9 g) were dissolved in tetrahydrofuran (200 ml). After gradually adding potassium tert-butoxide (6.70 g) while maintaining an internal temperature of 10° C. or below, the mixture was stirred at room temperature for 2.5 hours. The reaction solution was poured into water, and extraction with ethyl acetate was followed by washing with water. After drying with anhydrous magnesium sulfate, the solvent was distilled off under reduced pressure to produce a brown oily substance which was then purified by silica gel column chromatography (n-hexane:ethyl acetate=20:1) to give 4.73 g of 1-methoxy-4-(3-methoxymethylenecyclopentyl) benzene (48.4% yield).

1H-NMR(CDCl$_3$) δ ppm: (a mixture of E form and Z form) 1.55–1.76 (1H,m), 2.04–2.83 (5H,m), 2.94–3.10 (1H, m), 3.58 (3H, s), 3.78(3H,s), 5.93–5.95(1H,m), 6.84(2H,d, J=8.55 Hz), 7.16 (1H,d, J=8.55 Hz), 7.17, (1H,d, J=8.55 Hz).

REFERENCE EXAMPLE 31

1-Methoxy-4-(3-methoxymethylenecyclopentyl) benzene (4. 73 g) was dissolved in ethyl acetate (100 ml), 4 N HCl-ethyl acetate solution (10 ml) was added and the mixture was stirred at room temperature for 3 minutes. After washing the reaction solution with saturated sodium bicarbonate water and purified water, it was dried with anhydrous magnesium sulfate and the solvent was distilled off under reduced pressure to give 4. 30 g of 3-(4-methoxyphenyl) cyclopentane carboaldehyde (97.3%).

1H-NMR(CDCl$_3$) δ ppm: (a mixture of cis and trans) 1.56–2.43 (12H,m), 2.94–3.12(4H,m), 3.79(6H,s), 6.85(4H, d, J=8.55 Hz), 7.15(2H,d, J=8.55 Hz), 7.17(2H,d, J=8.55 Hz), 9.69 (1H,s), 9.70(1H,s).

REFERENCE EXAMPLE 32

3-(4-Methoxyphenyl) cyclopentane carboaldehyde (4.30 g) and benzylamine (2.49 g) were refluxed for 3 hours in benzene (100 ml) in the presence of p-toluenesulfonic acid (452 mg) using a Dean-Stark apparatus while removing the water generated. After distilling off the benzene under reduced pressure, it was dissolved in methanol (100 ml) while cooling on ice, sodium borohydride (890 mg) was gradually added and the mixture was stirred at room temperature for 18 hours. After concentrating the reaction solution, water was added, and extraction with chloroform was followed by washing with saturated sodium bicarbonate water and saturated saline. After drying with anhydrous magnesium sulfate, the solvent was distilled off under reduced pressure to produce a light yellow oily substance which was then purified by silica gel column chromatography (n-hexane:ethyl acetate=2:1→1:1→1:2) to give 5.60 g of N-benzyl-N[3-(4-methoxyphenyl)cyclopenylmethyl] amine (96.1% yield).

1H-NMR(CDCl$_3$) δ ppm:(a mixture of cis and trans) 1.21–2.34 (7H,m), 2.58–2.64(2H,m), 2.98–3.01(1H,m), 3.75(3H,s), 3.79(2H,s), 6.81(2H,d, J=7.94 Hz), 7.12(2H,d, J=7.94 Hz), 7.24–7.32(5H,m).

N-Benzyl-N-[3-(4-methoxyphenyl)cyclopentylmethyl] amine (free compound, 5.60 g) was dissolved in ethyl acetate (100 ml), 4 N HCl-ethyl acetate solution (10 ml) was added, and the mixture was stirred at room temperature for 2 hours. The deposited crystals were filtered and air-dried to give 6.30 g of N-benzyl-N-[3-(4-methoxyphenyl) cyclopentylmethyl]amine hydrochloride (quantitative yield).

REFERENCE EXAMPLE 33

N-Benzyl-N-[3-(4-methoxyphenyl)cyclopentylmethyl] amine hydrochloride (6.30 g) was dissolved in acetic acid (130 ml), and 10% palladium-carbon (1.1 g) was added. After substituting the reaction vessel with hydrogen gas, hydrogen addition was carried out at normal pressure, 80° C. for 2 hours. After the reaction, the catalyst was filtered off and the solvent was distilled off under reduced pressure to produce light yellow crystals which were then washed with diethyl ether to give 4.31 g of 3-(4-methoxyphenyl) cyclopentylmethylamine hydrochloride (94.0%).

1H-NMR(CD$_3$OD) δ ppm: (mixture of cis and trans) 1.19–2.49 (7H,m), 2.94–3.10(3H,m), 3.76(3H,s), 6.83(2H,d, J=8.55 Hz), 7.16(2H,d, J=8.55 Hz).

REFERENCE EXAMPLE 34

2-Cyclopenten-1-one (25.9 g) and cerium chloride heptahydrate (118 g) were dissolved in methanol (400 ml). After gradually adding sodium borohydride (12.6 g) while cooling on ice, the mixture was stirred at room temperature for 1.5 hours. The reaction solution was poured into ice water, and after extraction with ether and drying with anhydrous magnesium sulfate, the solvent was distilled off under reduced pressure to give 7.10 g of 2-cyclopenten-1-ol (26.7%).

1H-NMR(CD$_3$OD) δ ppm:1.56–1.73(2H,m), 2.18–2.35 (2H,m), 2.45–2.56(1H,m), 5.82–5.85(1H,m), 5.98–6.00(1H, m).

REFERENCE EXAMPLE 35

Palladium acetate (1.21 g), potassium acetate (31.7 g) and n-tetrabutylammonium chloride (31.2 g) were dissolved in acetonitrile (100 ml) under an argon air flow. After adding a solution of 2-cyclopenten-1-ol (9.03 g) in acetonitrile (80 ml) and a solution of ethyl 4-iodobenzoate (59.3 g) in acetonitrile (70 ml) in that order, the mixture was stirred at 60° C. for 28 hours. After adding a saturated aqueous solution of ammonium chloride, the mixture was filtered with cerite, extracted with diethyl ether and washed with saturated saline. After drying with anhydrous magnesium sulfate, the solvent was distilled off under reduced pressure to produce an oily substance which was then purified by silica gel column chromatography (n-hexane:ethyl acetate= 20:1) to give 7.29 g of ethyl 4-(3-oxocyclopentyl) benzoate (29.3% yield).

1H-NMR(CDCl$_3$) δ ppm:1.39(3H,t, J=7.32 Hz), 1.91–2.06(1H,m), 2.23–2.51(4H,m), 2.67(1H,dd, J=7.33, 17.7 Hz), 3.41–3.50(1H,m), 4.36(2H,q, J=7.32 Hz), 7.33 (2H,d, J=8.55 Hz), 8.02(2H,d, J=8.55 Hz).

REFERENCE EXAMPLE 36

3-(3-methoxyphenyl) cyclopentanone was obtained from ethyl acetoacetate and 3-methoxyphenacyl bromide according to the methods of Reference Examples 25 to 27.

1H-NMR(CDCl$_3$) δ ppm:1.90–2.06(1H,m), 2.22–2.51 (4H,m), 2.66(1H,dd, J=7.32, 18.3 Hz), 3.33–3.46(1H,m), 3.81(3H,s), 6.78–6.86(3H,m), 7.26(1H,m).

The following compounds were obtained by the methods in Reference Examples 28 to 29.

REFERENCE EXAMPLE 37

N-Benzyl-N-[3-(3-methoxyphenyl)cyclopentyl] amine

1H-NMR(CDCl$_3$) δ ppm: (a mixture of cis and trans) 1.42–2.16 (13H,m),2.30–2.40(1H,m), 2.92–3.05(1H,m), 3.19–3.36(3H,m), 3.74(6H,s), 3.77(4H,s), 6.69–6.85(6H,m), 7.15–7.31(12H,m).

REFERENCE EXAMPLE 38

3-(3-Methoxyphenyl)cyclopentylamine hydrochloride

1H-NMR(CD$_3$OD) δ ppm: (a mixture of cis and trans) 1.70–2.37, (11H,m) 2.48–2.58(1H,m), 3.00–3.20(1H,m), 3.31–3.38(1H,m), 3.71–3.85(4H,m), 6.74–6.88(6H,m), 7.20 (2H,t, J=7.94 Hz).

EXAMPLE 1

(2R)-2-(3-chlorophenyl)-2-hydroxy-N-[3-(3-methoxyphenyl)cyclohexyl]acetamide:diastereomer A (trans-H) and diastereomer B (trans-L)

To a solution of (trans)-3-(3-Methoxyphenyl) cyclohexylamine hydrochloride (5.40 g) in methylene chloride there were added (R)-(-)-m-chloromandelic acid (4.17 g), BOP reagent (9.88 g) and triethylamine (6.78 g), and the mixture was stirred overnight.

After terminating the reaction by addition of saturated saline to the reaction solution, extraction was performed with ethyl acetate, and after a series of washing with 1% hydrochloric acid, saturated sodium bicarbonate and saturated saline, the solution was dried with an hydrous magnesium sulfate The solvent was distilled off under reduced pressure to produce a crude product which was then separated and purified by silica gel column chromatography (n-hexane:ethyl acetate=4:1) to give 5.71 g of (2R)-2-(3-chlorophenyl)-2-hydroxy-N-[3-(3-methoxyphenyl) cyclohexyl]acetamide as a diastereomeric mixture (68.4% yield). Repeated silica gel column chromatography (n-hexane:ethyl acetate=4:1) allowed separation of the two diastereomers. Diastereomer A (trans-H) was obtained from the earlier eluted fraction and the diastereomer B (trans-L) was obtained from the later eluted fraction.

Diastereomer A(trans-H)1H-NMR(CDCl$_3$) δ ppm:1.45–2.00(8H,m), 2.40–2.49(1H,m), 3.79(3H,s), 4.20–4.26(1H,m), 5.01(1H,s), 6.60–6.75(4H,m), 7.17–7.31 (4H,m), 7.44(1H,s). Diastereomer B(trans-L)1H-NMR (CDCl$_3$) δ ppm:1.34–1.96(8H,m), 2.49–2.64 (1H,m), 3.79 (3H,s), 4.18–4.29(1H,m), 5.02(1H,s), 6.64–6.77 (4H,m), 7.18–7.31(4H,m), 7.45(1H,s).

EXAMPLE 2

(2R)-2-(3-Chlorophenyl)-2-hydroxy-N-[3-4(3-methoxyphenyl)cyclohexyl]acetamide:Diastereomer C (cis-H) and, Diastereomer D(cis-L)

Diastereomer C (cis-H) and diastereomer D (cis-L) were obtained from (cis)-3-(3-methoxyphenyl) cyclohexylamine hydrochloride and (R)-(−)-m-chloromandelic acid, according to the method of Example 1.

Diastereomer C(cis-H) 1H-NMR(CDCl$_3$) ppm:1.00–1.62 (4H,m), 1.70–2.18(4H,m), 2.53–2.74(1H,m), 3.79(3H,s), 4.00–4.25(1H,m), 4.94(1H,s), 6.23(1H,broad s), 6.70–6.78 (3H,m), 7.20–7.38(4H, m), 7.40(1H,s). Diastereomer D(cis-L) 1H-NMR(CDCl$_3$) δ ppm: 1.05–2.11(8H,m), 2.55–2.65 (1H,m), 3.78(3H,s), 3.70–4.02(1H,m), 4.93(1H,s), 6.31(1H, d,amide NH), 6.70–6.78(3H,m), 7.16–7.27 (4H, m) 7.38 (1H, s)

EXAMPLE 3

To a solution of diastereomer A obtained in Example 1, ((2R)-2-(3-chlorophenyl)-2-hydroxy-N-[3-(3-methoxyphenyl) cyclohexyl]acetamide) (2.79 g) in anhydrous tetrahydrofuran (85 ml) there was added dropwise at room temperature a tetrahydrofuran solution (11.5 ml) containing 2 M borane-dimethyl sulfide complex, and the mixture was refluxed for 2 hours. After adding methanol (10 ml) to the reaction solution to suspend the reaction and stirring for 30 minutes, 4 N HCl-ethyl acetate solution (5 ml) was added and stirring was continued for 30 minutes.

After concentrating the solvent under reduced pressure, it was dissolved in ethyl acetate and washed successively with a saturated aqueous sodium bicarbonate solution and saturated saline, and then dried with anhydrous magnesium sulfate. The solvent was distilled off under reduced pressure to produce a crude product which was then separated and purified by silica gel column chromatography (n-hexane:ethyl acetate=2:1) to give 2.15 g of (1R)-1-(3-chlorophenyl)-2-[3-(3-methoxyphenyl) cyclohexylamino]ethanol (trans-H) (79.9% yield).

1H-NMR(CDCl$_3$) δ ppm:1.41–1.95(8H,m), 2.50–3.08 (4H,m), 3.80(3H,s), 4.66(1H,dd, J=3.05, 9.16 Hz), 6.70–6.85(3H,m), 7.18–7.28(4H,m), 7.39(1H,s).

Elemental analysis: as $C_{21}H_{26}ClNO_2$ Calculated: C; 70.08, H; 7.28, N; 3.89 Found: C; 69.87, H; 7.33, N; 3.81 mp. 60–62° C., $[\alpha]_D$=−29.5° (c=1.01, CH$_3$OH).

After dissolving 320 mg of free bases in diethyl ether (10 ml) and adding 4 N HCl-ethyl acetate solution (5 ml), the mixture was stirred for 1.5 hours. The solvent was distilled off under reduced pressure to give 175 mg of (1R)-1-(3-chlorophenyl)-2-[3-(3-methoxyphenyl) cyclohexylamino] ethanol hydrochloride as colorless crystals (49.7% yield).

1H-NMR(CDCl$_3$) δ ppm:1.48–2.20(7H,m), 2.25–2.46 (1H,m), 2.85–3.10(1H,m), 3.20–3.60(3H,m), 3.73(3H,s), 5.40(1H,d, J=9.77 Hz), 5.70(1H,broad s), 6.62(1H,dd, J=2.44, 7.93 Hz), 6.77 (1H,dd, J=2.44, 7.93 Hz), 7.02–7.24 (4H,m), 7.35(1H,s), 8.17(1H,broad s,), 10.2(1H,broad s).

Elemental analysis: as $C_{21}H_{27}Cl_2NO_2$ Calculated: C; 63.64, H; 6.87, N; 3.53 Found: C; 63.73, H; 7.04, N; 3.48 mp. 158–159° C., $[\alpha]_D$=−45.2° (c=1.00, CH$_3$OH).

The compounds for Example 4 to 6 were synthesized according to the method of Example 3.

EXAMPLE 4

(1R)-1-(3-chlorophenyl)-2-[3-(3-methoxyphenyl) cyclohexylamino]ethanol hydrochloride (trans-L) was obtained from diastereomer B obtained in Example 1.

1H-NMR(CDCl$_3$) δ ppm:1.37–2.12(8H,m), 2.60–3.08 (4H,m), 3.80(3H,s), 4.65(1H,dd, J=3.66, 9.16 Hz), 6.70–6.83(3H,m), 7.18–7.25(4H,m), 7.39(1H,s).

EXAMPLE 5

(1R)-1-(3-Chlorophenyl)-2-[3-(3-methoxyphenyl) cyclohexylamino]ethanol (cis-H) was obtained from diastereomer C obtained in Example 2.

1H-NMR(CDCl$_3$) δ ppm:0.92–1.52(4H,m), 1.76–2.14 (4H,m), 2.46–2.69(3H,m), 3.01(1H,dd, J=3.66, 12.2 Hz), 3.80(3H,s), 4.60(1H,dd, J=3.66, 9.16 Hz), 6.68–6.84(3H,m), 7.14–7.30(4H,m), 7.37(1H,s).

EXAMPLE 6

(1R)-1-(3-Chlorophenyl)-2-[3-(3-methoxyphenyl) cyclohexylamino]ethanol (cis-L) was obtained from diastereomer D obtained in Example 2.

1H-NMR(CDCl$_3$) δ ppm:0.99–1.53(4H,m), 1.77–2.16 (4H,m), 2.45–2.70(3H,m), 3.00(1H,dd, J=3.66, 12.2 Hz), 3.80(3H,s), 4.61(1H,dd, J=3.66, 8.55 Hz), 6.69–6.81(3H,m), 7.16–7.28(4H,m), 7.37(1H,s).

EXAMPLE 7

A solution of the (1R)-1-(3-chlorophenyl)-2-[3-(3-methoxyphenyl) cyclohexylamino]ethanol (trans-H) obtained in Example 3 (2.21 g) in methylene chloride (100 ml) was cooled to −10° C. After slowly adding dropwise a solution of 1 M boron tribromide in methylene chloride thereto, the mixture was stirred for 2 hours while gradually heating it to room temperature. The reaction solution was poured a portion at a time into an aqueous sodium bicarbonate solution while cooling on ice in order to terminate the reaction, and the extraction was performed with a mixed solvent of chloroform:ethanol=5:1. After washing the organic layer with saturated saline, it was dried with anhydrous magnesium sulfate. The solvent was distilled off under reduced pressure to produce a crude product which was then separated and purified by silica gel column chromatography (chloroform-chloroform:methanol=20:1) to give 1.72 g of (1R)-1-(3-chlorophenyl)-2-[3-(3-hydroxyphenyl) cyclohexylamino]ethanol (trans-H) (81.1% yield).

1H-NMR(CDCl$_3$) δ ppm:1.35–1.96(8H,m), 2.60–3.03 (4H,m), 4.73 (1H,dd, J=3.66, 9.16 Hz), 6.59–6.79(3H,m), 7.07–7.28(4H,m), 7.35(1H,s).

The compounds for Embodiments 8 to 10 were synthesized according to the method of Embodiment 7.

EXAMPLE 8

(1R)-1-(3-Chlorophenyl)-2-[3-(3-hydroxyphenyl) cyclohexylamino]ethanol (trans-L) was obtained from the trans-L obtained in Example 4.

1H-NMR(CDCl$_3$) δ ppm:1.40–1.90(8H,m), 2.61–3.00 (4H,m), 4.74(1H,dd, J=3.05, 9.15 Hz), 6.64–6.74(3H,m), 7.10–7.25(4H,m), 7.32(1H,s).

EXAMPLE 9

(1R)-1-(3-Chlorophenyl)-2-[3-(3-hydroxyphenyl) cyclohexylamino]ethanol (cis-H) was obtained from the cis-H obtained in Example 5.

1H-NMR(CDCl$_3$) δ ppm:1.01–1.49(4H,m), 1.75–2.13 (4H,m), 2.44–2.74 (3H,m), 2.96 (1H, dd, J=3.66, 12.2 Hz), 4.68 (1H,dd, J=3.66, 9.16 Hz), 6.61–6.76(3H,m), 7.10–7.28 (4H,m), 7.34(1H,s).

EXAMPLE 10

(1R)-1-(3-Chlorophenyl)-2-[3-(3-hydroxyphenyl) cyclohexylamino]ethanol hydrochloride (cis-L) was obtained from the cis-L obtained in Embodiment 6.

1H-NMR(CDCl$_3$+CD$_3$OD) δ ppm:1.30–2.60(9H,m), 2.85–3.30 (3H,m), 5.14–5.22(1H,m), 6.65–6.71(3H,m), 7.08–7.16(1H,m), 7.28(3H,t), 7.36(1H,s), 7.44(1H,s).

EXAMPLE 11

(1R)-1-(3-Chlorophenyl)-2-[3-(3-ethoxycarbonylmethoxyphenyl)cyclohexylamino]ethanol hydrochloride (trans-H)

(Boc addition)

To a solution of the (1R)-1-(3-chlorophenyl)-2-[3-(3-hydroxyphenyl)cyclohexylamino]ethanol obtained in Example 7 (1.50 g) in dimethylformamide (30 ml) there were added a solution of 1 M di-tert-butylcarbonate in dimethylformamide (4.35 ml) and triethylamine (1.32 g), and the mixture was stirred overnight. Water was added to the reaction solution and extraction was performed with ethyl acetate. After washing the organic layer 3 times with water and once with saturated saline, it was dried with anhydrous magnesium sulfate. The solvent was distilled off under reduced pressure to produce a crude product which was then separated and purified by silica gel chromatography (n-hexane:ethyl acetate=4:1) to give 1.28 g of (2R)-3-[3-[[2-(3-chlorophenyl)-2-hydroxy-N-tert-butoxycarbonyl]ethylamino]cyclohexyl]phenol (trans-H) (66.4% yield).

(Alkylation)

To a solution of the (2R)-3-[3-[[2-(3-chlorophenyl)-2-hydroxy-N-tert-butoxycarbonyl]ethylamino]cyclohexyl]phenol (1.28 g) in acetone (50 ml) there were added anhydrous potassium carbonate (1.99 g) and ethyl bromoacetate (965 mg), and the mixture was refluxed for 2 hours. After the reaction, the deposited salt was filtered off and the solvent was concentrated under reduced pressure. The resulting crude product was separated and purified by silica gel column chromatography (n-hexane:ethyl acetate=3:1 to 1:1) to give 1.49 g of (2R)-ethyl[3-[3-[[2-(3-chlorophenyl)-2-hydroxy-N-tert-butoxycarbonyl]ethylamino]cyclohexyl]phenoxy]acetate (trans-H) (97.4% yield).

(Boc removal)

After dissolving (2R)-ethyl[3-[3-[[2-(3-chlorophenyl)-2-hydroxy-N-tert-butoxycarbonyl]ethylamino]cyclohexyl]phenoxy]acetate (1.49 g) in ethyl acetate (5 ml), 4 N HCl-ethyl acetate solution (20 ml) was added and the mixture was stirred for 2.5 hours at room temperature. The reaction solution was rendered alkaline with a saturated aqueous sodium bicarbonate solution and extracted with ethyl acetate. The organic layer was washed with saturated saline and then dried with anhydrous magnesium sulfate. After distilling off the solvent under reduced pressure, it was dissolved in diethyl ether (5 ml) and ethyl acetate (5 ml), 4 N HCl-ethyl acetate solution (10 ml) was added, and the mixture was stirred overnight at room temperature. The reaction solution was concentrated under reduced pressure to produce crude crystals which were then washed with isopropyl ether to give 1.05 g of (1R)-1-(3-chlorophenyl)-2-[3-(3-ethoxycarbonylmethoxyphenyl) cyclohexylamino] ethanol hydrochloride (trans-H) (79.9% yield).

1H-NMR(CDCl$_3$) δ ppm (free compound):1.30(3H,t, J=7.32 Hz), 1.37–1.98(8H,m), 2.61–3.11(6H,m), 4.27(2H,q, J=7.32 Hz), 4.60(2H,s), 4.71(1H,dd, J=3.66, 9.16 Hz), 6.67–6.72(1H,m), 6.81–6.87(2H,m), 7.20–7.26(4H,m), 7.40(1H,s).

Elemental analysis: as C$_{24}$H$_{31}$Cl$_2$NO$_4$ Calculated: C; 61.54,H; 6.67, N; 2.99. Found: C; 61.34, H; 6.68, N; 2.72. mp.137–138° C., [α]$_D$=−29.1°, (c=1.01,CHCl$_3$).

The compounds for Example 12 to 14 were synthesized according to the method of Example 11.

EXAMPLE 12

(1R)-1-(3-Chlorophenyl)-2-[3-(3-ethoxycarbonylmethoxyphenyl)cyclohexylamino]ethanol(trans-L)

1H-NMR(CDCl$_3$) δ ppm:1.29(3H,t, J=6.70 Hz), 1.36–1.97(8H,m), 2.59–3.02(6H,m), 4.27(2H,q, J=6.70 Hz), 4.60(2H,s), 4.67 (1H,dd, J=3.66, 9.16 Hz), 6.65–6.72(1H, m), 6.80–6.86(2H,m), 7.10–7.27(4H,m), 7.38(1H,s).

EXAMPLE 13

(1R)-1-(3-Chlorophenyl)-2-[3-(3-ethoxycarbonylmethoxyphenyl)cyclohexylamino]ethanol(cis-H)

1H-NMR(CDCl$_3$) δ ppm:0.98–1.47(4H,m), 1.28(3H,t, J=7.30 Hz), 1.80–2.13(4H,m), 2.45–3.00(6H,m), 4.26(2H,q, J=7.30 Hz), 4.59(2H,s), 4.58–4.68(1H,m), 6.69–6.83(3H, m), 7.15–7.28(4H,m), 7.36(1H,s).

EXAMPLE 14

(1R)-1-(3-Chlorophenyl)-2-[3-(3-ethoxycarbonylmethoxyphenyl)cyclohexylamino]ethanol(cis-L)

1H-NMR(CDCl$_3$) δ ppm:0.98–1.51(4H,m), 1.30(3H,t, J=7.30 Hz), 1.78–2.18(4H,m), 2.43–3.01(6H,m), 4.27(2H,q, J=7.30 Hz), 4.60(2H,s), 4.58–4.68(1H,m), 6.68–6.80(2H, m), 6.83(1H,d, J=7.30 Hz), 7.17–7.26(4H,m), 7.36(1H,s).

EXAMPLE 15

Sodium (2R)-[3-[3-[2-(3-chlorophenyl)-2-hydroxyethylamino]cyclohexyl]phenoxy]acetate (trans-H)

To a solution of the trans-H obtained to the method of Example 11, (1R)-1-(3-chlorophenyl)-2-[3-(3-ethoxycarbonylmethoxyphenyl) cyclohexylamino]ethanol (free base) (527 mg) in methanol (15 ml) there was added 1 N sodium hydroxide solution (1.16 ml), and the mixture was stirred at room temperature for 2 hours. After concentrating the reaction solution under reduced pressure (repeated azeotropy with toluene), it was washed with diethyl ether to give 351 mg of sodium (2R)-[3-[3-[2-(3-chlorophenyl)-2-hydroxyethylamino]cyclohexyl]phenoxy]acetate (trans-H) as a pale yellow powder (67.5% yield).

1H-NMR(CD$_3$OD) δ ppm:1.47–1.98(8H,m), 2.68–2.88 (3H,m) 3.00 (1H,broad s), 4.37(2H,s), 4.75–4.77(1H,m), 6.68–6.84(3H,m), 7.10–7.38(4H,m), 7.42(1H,s).

The following compounds were synthesized according to the methods of Examples 1 to 15.

EXAMPLE 16

(2R)-2-(3-Chlorophenyl)-2-hydroxy-N-[3-(4-methoxyphenyl)cyclohexyl]acetamide (trans-H)

1H-NMR(CDCl$_3$) δ ppm:1.34–1.96(8H,m), 2.31–2.43 (1H,m), 3.75(1H,d, J=4.27 Hz), 3.78(3H,s), 4.23–4.26(1H, m),5.03 (1H,d, J=4.27 Hz), 6.47(1H,broad d, J=7.32 Hz), 6.82(2H,d, J=8.55 Hz),7.03(2H,d, J=8.55 Hz), 7.32–7.33 (3H,m), 7.4$_5$(1H,s).

EXAMPLE 17

(2R)-2-(3-Chlorophenyl)-2-hydroxy-N-[3-(4-methoxyphenyl)cyclohexyl]acetamide (trans-L)

1H-NMR(CDCl$_3$) δ ppm: 1.31–1.96(8H,m), 2.50–2.61 (1H,m), 3.70–3.71(1H,m),3.78(3H,s), 4.22–4.27(1H,m), 5.03(1H,d, J=3.66 Hz), 6.60(1H,broad d, J=7.32 Hz), 6.83 (2H,d, J=8.55 Hz), 7.08(2H,d, J=8.55 Hz), 7.31–7.32(3H, m), 7.46(1H,s).

EXAMPLE 18

(2R)-2-(3-Chlorophenyl)-2-hydroxy-N-[3-(4-methoxyphenyl)cyclohexyl]acetamide(cis-H)

1H-NMR(CDCl$_3$) δ ppm:1.09–1.57(4H,m), 1.77–2.10 (4H,m), 2.54–2.63(1H,m), 3.62(1H,d, J=4.27 Hz), 3.78(3H, s), 3.81–3.97 (1H,m),4.96(1H,d, J=3.66 Hz), 6.01(1H,broad d, J=7.94 Hz), 6.82(2H,d, J=8.55 Hz), 7.08(2H,d, J=8.55 Hz), 7.27–7.28(3H,m), 7.39(1H,s).

EXAMPLE 19

(2R)-2-(3-Chlorophenyl)-2-hydroxy-N-[3-(4-methoxyphenyl)cyclohexyl]acetamide(cis-L)

1H-NMR(CDCl$_3$) δ ppm: 1.06–1.60(4H,m), 1.79–2.14 (4H,m), 2.54–2.66(1H,m), 3.54–3.56(1H,m), 3.78(3H,s), 3.81–3.98 (1H,m), 4.97(1H,d, J=3.66 Hz), 6.07(1H,broad d, J=3.05 Hz), 6.82(2H,d, J=8.55 Hz), 7.09(2H,d, J=8.55 Hz), 7.27–7.28(3H,m), 7.39(1H,s).

EXAMPLE 20

(1R)-1-(3-Chlorophenyl)-2-[3-(4-methoxyphenyl) cyclohexylamino]ethanol(trans-H), 1H-NMR(CDCl$_3$) δ ppm:1.37–1.91(8H,m), 2.62(1H,dd, J=8.55, 12.2 Hz), 2.77–2.90(1H,m), 2.96(1H,dd, J=3.66, 12.2 Hz), 3.02–3.05(1H,m), 3.79(3H,s), 4.64(1H,dd, J=3.66, 8.55 Hz), 6.84(2H,d, J=9.16 Hz), 7.14(2H,d, J=9.16 Hz), 7.25–7.26(3H,m), 7.40(1H,s).

EXAMPLE 21

(1R)-1-(3-Chlorophenyl)-2-[3-(4-methoxyphenyl) cyclohexylamino]ethanol(trans-L)

1H-NMR(CDCl$_3$) δ ppm:1.36–1.93(8H,m), 2.62(1H,dd, J=8.55, 12.2 Hz), 2.73–2.87(1H,m), 2.97(1H,dd, J=3.66, 12.2 Hz), 3.02–3.05(1H,m), 3.79(3H,s), 4.65(1H,dd, J=3.66, 8.55 Hz), 6.85(2H,d, J=8.55 Hz), 7.13(2H,d, J=8.55 Hz), 7.25–7.26(3H,m), 7.40(1H,s).

EXAMPLE 22

(1R)-1-(3-Chlorophenyl)-2-[3-(4-methoxyphenyl) cyclohexylamino]ethanol (cis-H)

1H-NMR(CDCl$_3$) δ ppm:0.98–1.51(4H,m), 1.79–2.16 (4H,m), 2.46–2.70(3H,m), 3.02(1H,dd, J=3.66, 12.2 Hz), 3.79(3H,s), 4.61(1H,dd, J=3.66, 8.55 Hz), 6.84(2H,d, J=8.55 Hz), 7.11(2H,d, J=8.55 Hz), 7.23–7.25(3H,m), 7.37(1H,s).

EXAMPLE 23

(1R)-1-(3-Chlorophenyl)-2-[3-(4-methoxyphenyl) cyclohexylamino]ethanol (cis-L)

1H-NMR(CDCl$_3$) δ ppm:1.00–1.51(4H,m), 1.78–2.17 (4H,m), 2.44–2.71(3H,m), 3.00(1H,dd, J=3.66, 12.2 Hz), 3.79(3H,s), 4.61(1H,dd, J=3.66, 8.54 Hz), 6.84(2H,d, J=8.55 Hz), 7.12(2H,d, J=8.55 Hz), 7.21–7.25(3H,m), 7.37(1H,s).

EXAMPLE 24

(1R)-1-(3-Chlorophenyl)-2-[3-(4-hydroxyphenyl) cyclohexylamino]ethanol(trans-H)

1H-NMR(CDCl$_3$) δ ppm:1.37–1.91(8H,m), 2.66(1H,dd, J=9.16, 12.2 Hz), 2.74–2.88(1H,m), 2.94(1H,dd, J=3.66, 12.2 Hz), 3.00–3.07(1H,m), 3.30(3H,broad s), 4.68(1H,dd, J=3.66, 9.16 Hz), 6.75(2H,d, J=8.55 Hz), 7.06(2H,d, J=8.55 Hz), 7.23–7.25(3H,m), 7.39(1H,s).

EXAMPLE 25

(1R)-1-(3-Chlorophenyl)-2-[3-(4-hydroxyphenyl) cyclohexylamino]ethanol(trans-L)

1H-NMR(CDCl$_3$) δ ppm:1.36–1.93(8H,m), 2.65(1H,dd, J=8.55, 12.2 Hz), 2.71–2.84(1H,m), 2.96(1H,dd, J=3.66, 12.2 Hz), 3.00–3.06(1H,m), 3.30(3H,broad s), 4.67(1H,dd, J=3.66, 8.55 Hz), 6.75(2H,d, J=8.55 Hz), 7.06(2H,d, J=8.55 Hz), 7.23–7.25(3H,m), 7.38(1H,s).

EXAMPLE 26

(1R)-1-(3-Chlorophenyl)-2-[3-(4-hydroxyphenyl) cyclohexylamino]ethanol (cis-H)

1H-NMR(CDCl$_3$) δ ppm:1.04–1.51(4H,m), 1.69–2.10 (4H,m), 2.33–3.02(4H,m), 3.90(3H,broad s), 4.79(1H,dd, J=2.44, 9.16 Hz), 6.73(2H,d, J=8.54 Hz), 6.93(2H,d, J=8.54 Hz), 7.13–7.23(3H,m), 7.34(1H,s).

EXAMPLE 27

(1R)-1-(3-Chlorophenyl)-2-[3-(4-hydroxyphenyl) cyclohexylamino]ethanol(cis-L)

1H-NMR(CDCl$_3$+CD$_3$OD) δ ppm:1.00–1.54(4H,m), 1.76–2.14, (4H,m), 2.40–2.96(4H,m), 4.66–4.75(1H,m), 6.74–6.77(2H,m), 7.00–7.05(2H,m), 7.25(3H,broad s), 7.37 (1H,s).

EXAMPLE 28

(1R)-1-(3-Chlorophenyl)-2-[3-(4-ethoxycarbonylmethoxyphenyl)cyclohexylamino] ethanol hydrochloride (trans-H)

1H-NMR(CD$_3$OD) δ ppm:1.27(3H,t, J=7.32 Hz), 1.68–1.96(6H,m), 2.00–2.24(2H,m), 2.96–3.06(1H,m), 3.10 (1H,dd, J=10.4, 12.8 Hz), 3.25–3.26(1H,m), 3.50–3.59(1H, m), 4.23(2H,q, J=7.32 Hz), 4.66(2H,s), 5.00 (H,dd, J=3.05, 10.4 Hz), 6.88(2H,d, J=9.16 Hz), 7.23(2H,d, J=9.16 Hz), 7.33–7.39(3H,m), 7.50(1H,s).

EXAMPLE 29

(1R)-1-(3-Chlorophenyl)-2-[3-(4-ethoxycarbonylmethoxyphenyl)cyclohexylamino] ethanol hydrochloride(trans-L)

1H-NMR(CD$_3$OD) δ ppm:1.27(3H,t, J=7.32 Hz) 1.68–1.95(6H,m), 2.03–2.23(2H,m), 2.95–3.05(1H,m), 3.10 (1H,dd, J=10.4, 12.2 Hz), 3.22–3.30(1H,m), 3.49–3.58(1H, m), 4.23(2H,q, J=7.32 Hz), 4.66(2H,s), 4.98(1H,dd, J=3.05, 10.4 Hz), 6.88(2H,d, J=8.55 Hz), 7.23(2H,d, J=8.55 Hz), 7.33–7.39(3H,m), 7.50(1H,s).

EXAMPLE 30

(1R)-1-(3-Chlorophenyl)-2-[3-(4-ethoxycarbonylmethoxyphenyl)cyclohexylamino] ethanol (cis-H)

1H-NMR(CDCl$_3$) δ ppm:1.10–1.50(4H,m), 1.32(3H,t, J=6.72 Hz), 1.76–2.22(4H,m), 2.41–2.58(1H,m), 2.67–2.83 (2H,m), 2.83–3.20 (3H,m), 4.27(2H,q, J=6.72 Hz), 4.58(2H, s), 4.81(1H,dd, J=3.06, 9.16 Hz), 6.82(2H,d, J=8.55 Hz), 7.09(2H,d, J=8.55 Hz), 7.20–7.30 (3H,m), 7.38(1H,s).

EXAMPLE 31

(1R)-1-(3-Chlorophenyl)-2-[3-(4-ethoxycarbonylmethoxyphenyl)cyclohexylamino]ethanol(cis-L)

1H-NMR(CDCl₃) δ ppm:1.05–1.53(4H,m), 1.30(3H,t, J=7.33 Hz), 1.77–2.75(9H,m), 2.99–3.08(1H,m), 4.27(2H,q, J=7.33 Hz), 4.59(2H,s), 4.70(1H,dd, J=3.05, 9.15 Hz), 6.83 (2H,d, J=6.72 Hz), 7.11(2H,d, J=6.72 Hz), 7.18–7.30(3H, m), 7.37(1H,s).

EXAMPLE 32

Sodium (2R)-(4-[3-[2-(3-chlorophenyl)-2-hydroxyethylamino]cyclohexyl]phenoxy) acetate (trans-H)

EXAMPLE 33

(1R)-1-(3-Chlorophenyl)-2-[3-(2-methoxyphenyl)cyclohexylamino]ethanol (trans-H)

1H-NMR(CDCl₃) δ ppm:1.39–2.06(8H,m), 2.55–2.75 (1H,m), 2.98–3.15(2H,m), 3.25–3.45(1H,m), 3.82(3H,s), 4.61–4.78(1H,m), 6.80–7.01(2H,m), 7.13–7.38(5H,m), 7.42 (1H,s).

EXAMPLE 34

(1R)-1-(3-Chlorophenyl)-2-[3-(2-methoxyphenyl)cyclohexylamino]ethanol (trans-L)

1H-NMR(CDCl₃) δ ppm:1.40–2.08(8H,m), 2.60–2.80 (1H,m), 2.94–3.16(2H,m), 3.24–3.43(1H,m), 3.82(3H,s), 4.61–4.78(1H,m), 6.80–7.03(2H,m), 7.11–7.36(5H,m), 7.42 (1H,s).

EXAMPLE 35

(1R)-1-(3-Chlorophenyl)-2-[3-(2-methoxyphenyl)cyclohexylamino]ethanol hydrochloride (cis-H)

1H-NMR(CDCl₃) δ ppm:1.33–1.50(2H,m), 1.57–1.98 (6H,m), 2.22–2.41(2H,m), 2.88–3.34(4H,m), 3.78(3H,s), 5.36(1H,d like), 6.74–6.84(2H,m), 7.05–7.29(5H,m), 7.42 (1H,s), 8.56(1H,br s), 10.02(1H,br s).

EXAMPLE 36

(1R)-1-(3-Chlorophenyl)-2-[3-(2-methoxyphenyl)cyclohexylamino]ethanol hydrochloride(cis-L)

1H-NMR(CDCl₃) δ ppm:1.40–1.71(4H,m), 1.80–1.91 (1H,m), 1.96–2.08(1H,m), 2.20–2.35(1H,m), 2.90–3.31(4H, m), 3.82(3H,s), 5.20(1H,dd, J=10.38, 2.44 Hz), 6.83–6.96 (2H,m), 7.13–7.33(5H,m), 7.44(1H,s).

EXAMPLE 37

(1R)-1-(3-Chlorophenyl)-2-[3-(2-hydroxyphenyl)cyclohexylamino]ethanol (trans-H)

1H-NMR(CDCl₃) δ ppm:1.40–2.10(9H,m), 2.78(1H,dd, J=12.21, 9.16 Hz), 2.91(1H,dd, J=12.21, 3.05 Hz), 3.03–3.11(1H,m), 3.20–3.35(1H,m), 4.80(1H,dd, J=9.16, 3.66 Hz), 6.68–6.75(1H,m), 6.80–6.91(1H,m), 7.00–7.28 (5H,m), 7.35(1H,s).

EXAMPLE 38

(1R)-1-(3-Chlorophenyl)-2-[3-(2-hydroxyphenyl)cyclohexylamino]ethanol (trans-L)

1H-NMR(CDCl₃) δ ppm:1.40–2.10(8H,m), 2.69–3.10 (4H,m), 2.75(1H,dd, J=12.21, 9.77 Hz), 2.88(1H,dd, J=15.29, 3.66 Hz), 3.15–3.33(1H,m), 4.72(1H,dd, J=9.46, 3.66 Hz), 6.79 (1H,dd, J=7.93, 1.22 Hz), 6.83–6.90(1H,m), 7.04(1H,dd, J=7.93, 1.83 Hz), 7.10–7.18(1H,m), 7.20–7.33 (3H,m), 7.39(1H,s).

EXAMPLE 39

(1R)-1-(3-Chlorophenyl)-2-[3-(2-hydroxyphenyl)cyclohexylamino]ethanol(cis-H)

1H-NMR(CDCl₃) δ ppm:1.09–1.54(4H,m), 1.75–2.20 (4H,m), 2.64–3.05(4H,m), 4.74(1H,dd, J=9.63, 3.66 Hz), 6.73–6.88(2H,m), 6.98–7.05(1H,m), 7.09–7.16(1H,m), 7.20–7.30(3H,m), 7.37 (1H,s).

EXAMPLE 40

(1R)-1-(3-Chlorophenyl)-2-[3-(2-hydroxyphenyl)cyclohexylamino]ethanol (cis-L)

1H-NMR(CDCl₃) δ ppm:1.20–1.53(4H,m), 1.64–1.93 (2H,m), 2.00–2.14(1H,m), 2.23–2.36(1H,m), 2.70–3.14(4H, m), 5.14, (1H,d like), 6.73–6.88(2H,m), 6.93–7.03(2H,m), 7.13–7.26 (3H,m), 7.38(1H,s).

EXAMPLE 41

(1R)-1-(3-Chlorophenyl)-2-[3-(2-ethoxycarbonylmethoxyphenyl)cyclohexylamino]ethanol (trans-H)

1H-NMR(CDCl₃) δ ppm:1.25(3H,t, J=7.32 Hz), 1.57–1.83(4H,m), 1.93–2.25(3H,m), 2.40–2.55(1H,m), 2.87–3.00(1H,m), 3.43–3.73 (3H,m), 4.07–4.23(2H,m), 4.53(1H,d, J=16.48 Hz), 4.84(1H,d, J=16.48 Hz), 5.59(1H,d like), 5.94(1H,br s), 6.63(1H,d, J=7.93 Hz), 6.91(1H,t, J=7.32 Hz), 7.03–7.33(5H,m), 7.45(1H,s), 8.42(1H,br s), 9.84(1H,br s). [α]$_D$=−13.5° (c=0.30,CHCl₃)

EXAMPLE 42

(1R)-1-(3-Chlorophenyl)-2-[3-(2-ethoxycarbonylmethoxyphenyl)cyclohexylamino]ethanol(trans-L)

1H-NMR(CDCl₃) δ ppm:1.27(3H,t, J=7.32 Hz), 1.57–2.55(8H,m), 3.18–3.63(4H,m), 4.18(2H,q, J=7.32 Hz), 4.64(1H,d, J=16.48 Hz), 4.81(1H,d, J=16.48 Hz), 5.56(1H, br s), 6.00(1H,br s), 6.66(1H,d, J=7.93 Hz), 6.93(1H,t, J=7.93 Hz), 7.07–7.35(5H,m), 7.46(1H,s), 8.02(1H,br s), 10.28(1H,br s). [α]$_D$=−6.8° (c=0.31,CHCl₃)

EXAMPLE 43

(1R)-(3-Chlorophenyl)-2-[3-(2-ethoxycarbonylmethoxyphenyl)cyclohexylamino]ethanol hydrochloride (cis-H)

1H-NMR(CDCl₃) δ ppm:1.00–1.60(4H,m), 1.28(3H,t, J=7.32 Hz), 1.80–2.25(4H,m), 2.40–2.80(2H,m), 2.96–3.18, (2H,m), 4.24(2H,q, J=7.32 Hz), 4.56–4.73(3H,m), 6.65–6.76, (1H,m), 6.90–7.00(1H,m), 7.08–7.33(5H,m), 7.37(1H,s). [α]$_D$=−24.5° (c=0.25,CHCl₃)

EXAMPLE 44

(1R)-1-(3-Chlorophenyl)-2-[3-(2-ethoxycarbonylmethoxyphenyl)cyclohexylamino]ethanol hydrochloride (cis-L)

1H-NMR(CDCl₃) δ ppm:1.24(3H,t, J=7.32 Hz), 1.38–2.00,(6H,m), 2.27–2.50(2H,m), 2.97–3.37(4H,m), 4.05–4.23, (2H,m), 4.58(2H,s), 5.38(1H,m), 5.57(1H,br s), 6.67(1H,d, J=7.93 Hz), 6.89(1H,t, J=7.93 Hz), 7.05–7.30 (5H,m), 7.43(1H,s), 8.52(1H,br s), 10.02(1H,br s) $[\alpha]_D$=+9.4° (c=0.11, CHCl$_3$)

EXAMPLE 45

Sodium (2R)-(2-[3-[2-(3-chlorophenyl)-2-hydroxyethylamino]cyclohexyl]phenoxy)acetate (trans-H)

1H-NMR(CD$_3$OD) δ ppm:1.10–1.64(4H,m), 1.75–2.20 (4H,m), 2.72–3.00(3H,m), 3.24(1H,m), 4.39(2H,s), 4.43 (1H,dd, J=9.76, 3.66 Hz), 6.74–6.90(2H,m), 7.00–7.36(5H, m), 7.41(1H,s).

EXAMPLE 46

To a solution of the trans-H compound, (1R)-1-(3-chlorophenyl)-2-[3-(3-ethoxycarbonylmethoxyphenyl) cyclohexylamino]ethanol (hydrochloride), obtained in Example 11 (220 mg) in ethanol (10 ml) there was added 1 N sodium hydroxide solution (2.5 ml), and the mixture was stirred at room temperature for 2 hours. After concentrating the reaction solution under reduced pressure, water (2 ml) was added, and after adding 1 N aqueous solution of hydrochloric acid (2.03 ml) while stirring and cooling on ice, the deposited crystals were filtered off and dried to give 153 mg of (2R)-(3-[3-[2-(3-chlorophenyl)-2-hydroxyethylamino]cyclohexyl]phenoxy) acetic acid (trans-H) as a white crystalline powder (81% yield).

EXAMPLE 47

2-Methoxyethylamine (320 mg) was added to the (1R)-1-(3-chlorophenyl)-2-[3-(4-ethoxycarbonylmethoxyphenyl) cyclohexylamino]ethanol hydrochloride (trans-H) obtained in Example 28 (100 mg), and the mixture was stirred at room temperature for 71 hours. The reaction solution was separated and purified by silica gel column chromatography (chloroform:methanol=10:1) to obtain 97 mg of (2R)-2-[4-[3-[2-(3-chlorophenyl)-2-hydroxyethylamino]cyclohexyl] phenoxy]-N-(2-methoxyethyl) acetamide (90% yield).

1H-NMR(CDCl$_3$) δ ppm:1.36–1.90(8H,m), 2.58(2H, broad s), 2.64(1H,dd, J=9.16, 12.2 Hz), 2.78–2.90(1H,m), 2.93(1H,dd, J=3.66, 12.2 Hz), 2.99–3.13(1H,m), 3.36(3H,s), 3.42–3.58(4H,m), 4.46(2H,s), 4.66(1H,dd, J=3.66, 9.16 Hz), 6.85(2H,d, J=8.55 Hz), 6.97(1H,broad s), 7.15(2H,d, J=8.55 Hz), 7.23–7.27(3H,m), 7.40(1H,s).

EXAMPLE 48

(2R)-2-[4-[3-[2-(3-Chlorophenyl)-2-hydroxyethylamino] cyclohexyl]phenoxy]-N-ethylacetamide was obtained from the compound of Example 28 and ethylamine, according to the method of Example 47.

1H-NMR(CDCl$_3$) δ ppm:1.19(3H,t, J=7.32 Hz), 1.39–2.16(8H,m), 2.78(1H,dd, J=9.77, 12.2 Hz), 2.96–3.15 (1H,m), 3.24(1H,broad s), 3.40(2H,q, J=7.32 Hz), 4.40(2H, s), 4.47(1H,broad s), 4.58 (1H,broad s), 4.97(1H,dd, J=3.05, 9.77 Hz), 6.61(1H,broad s), 6.78(2H,d, J=8.55 Hz), 7.14 (2H,d, J=8.55 Hz), 7.23–7.27(3H,m), 7.37(1H,s).

EXAMPLE 49

(2R)-2-[4-[3-[2-(3-Chlorophenyl)-2-hydroxyethylamino] cyclohexyl]phenoxy]-1-piperidin-1-yl ethanone was obtained from the compound of Example 28 and piperidine, according to the method of Example 47.

1H-NMR(CDCl$_3$) δ ppm:1.36–1.90(14H,m), 2.62(1H,dd, J=9.16, 12.2 Hz), 2.66(2H,broad s), 2.75–2.88(1H,m), 2.93 (1H,dd, J=3.66, 12.2 Hz), 2.98–3.08(1H,m), 3.48–3.56(4H, m), 4.63(2H,s), 4.67(1H,d, J=3.66 Hz), 6.77(2H,d, J=8.55 Hz), 7.12 (2H,d, J=8.55 Hz), 7.25–7.27(3H,m), 7.40(1H,s).

EXAMPLE 50

(2R)-2-[4-[3-[2-(3-Chlorophenyl)-2-hydroxyethylamino] cyclohexyl]phenoxy]-N-(2-methoxyethyl) acetamide was obtained from the compound of Example 30, (1R)-1-(3-chlorophenyl)-2-[3-(4-ethoxycarbonylmethoxyphenyl) cyclohexylamino]ethanol (cis-H) and 2-methoxyethylamine, according to the method of Example 47.

1H-NMR(CDCl$_3$) δ ppm:1.00–1.52(4H,m), 1.76–2.40 (6H,m), 2.40–2.73(3H,m), 3.01(1H2dd, J=3.66, 12.2 Hz), 3.34(3H,s), 3.41–3.60(4H,m), 4.47(2H,s), 4.63(1H,dd, J=3.66, 9.15 Hz), 6.85(2H,d, J=8.55 Hz), 6.94(1H,broad s), 7.13(2H,d, J=8.55 Hz), 7.19–7.28 (3H,m), 7.37(1H,s)

EXAMPLE 51

(2R)-Ethyl [4-[3-[2-(3-chlorophenyl)-2-hydroxyethylamino]cyclohexyl]phenoxy]malonate was obtained from the compound of Example 26 according to the method of Example 11, using ethyl bromomalonate as the alkylating agent.

1H-NMR(CDCl$_3$) δ ppm:1.23–1.94(13H,m), 2.15–2.34 (2H,m), 2.42–2.58(1H,m), 2.90–3.22(2H,m), 4.27–4.36(4H, m), 5.08(2H,broad s)m5.13(1H,s ), 4.22(1H,d, J=6.10 Hz), 6.83(1H,d, J=8.55 Hz), 7.04–7.08(3H,m), 7.23–7.27(3H,m), 7.41(1H,s).

EXAMPLE 52

Acetic acid (1 ml) and PtO$_2$ (160 mg) were added to a solution of (R)-2-amino-1-(3-chlorophenyl) ethanol (600 mg) and 4-phenylcyclohexanone (610 mg) in methanol (30 ml), and hydrogen addition was carried out at room temperature. After consumption of the starting materials, the catalyst was filtered off and the filtrate was concentrated under reduced pressure. Separation and purification by silica gel column chromatography (chloroform:methanol=30:1) gave 43 mg of (1R)-1-(3-chlorophenyl)-2-(4-phenylcyclohexylamino) ethanol (4.0% yield).

1H-NMR(CDCl$_3$) δ ppm: 1.04–1.56 (4H,m), 1.80–2.05 (4H,m), 2.37–3.95 (4H,m), 4.69 (1H,dd), 7.11–7.30 (8H,m), 7.39 (1H,s). Also obtained was 65 mg of the dechlorinated form, (1R)-1-phenyl-2-(4-phenylcyclohexylamino)ethanol (6.3% yield).

1H-NMR(CDCl$_3$) δ ppm:1.57–1.90(8H,m), 2.50–2.73 (3H,m), 2.90–3.00(2H,m), 4.70(1H,dd), 7.12–7.22(10H,m).

EXAMPLE 53

To a solution of (R)-2-amino-1-(3-chlorophenyl)ethanol (686 mg) and 3-(3-ethoxycarbonylaethoxyphenyl) cyclohexanone (1.1 g) in methanol (35 ml) there were added sodium cyanoborohydride (377 mg) and acetic acid (1.2 ml) at room temperature, and the mixture was stirred overnight. To this solution there was then added concentrated hydrochloric acid (2 ml) while stirring on ice. After 2 hours of stirring, water and ammonia water were added, and once alkalinity was reached extraction was performed with ethyl acetate. After drying the organic layer with anhydrous magnesium sulfate, the solvent was distilled off under reduced pressure. The residue was separated and purified by silica gel column chromatography (ethyl acetate:hexane= 5:1) to give 1.23 g of (1R)-1-(3-chlorophenyl)-2-[3-(3-ethoxycarbonylmethoxyphenyl) cyclohexylamino]ethanol as a colorless oily substance (71% yield).

1H-NMR(CDCl$_3$) δ ppm:1.30(3H,t, J=7.32 Hz), 1.37–1.98(8H,m), 2.61–3.11(6H,m), 4.27(2H,q, J=7.32 Hz), 4.60(2H,s), 4.71 (1H,dd, J=3.66, 9.16 Hz), 6.67–6.72(1H, m), 6.81–6.87(2H,m), 7.20–7.26(4H,m), 7.40(1H,s).

EXAMPLE 54

To a solution of (2R)-(3-[3-[2-(3-chlorophenyl)-2-hydroxyethylamino]cyclohexyl]phenoxy)acetic acid (trans-H) obtained in Example 46 (1.0 g) in methanol (10 ml) there was added an excess of diazomethane in ether solution, and the mixture was stirred at room temperature for 30 minutes. After distilling off the solvent under reduced pressure, separation and purification by silica gel column chromatography (ethyl acetate:hexane=5:1) gave 0.91 g of (1R)-1-(3-chlorophenyl)-2-[3-(3-methoxycarbonylmethoxyphenyl) cyclohexylamino]ethanol (88% yield).

The following compounds were produced according to the methods of Examples 1 to 3.

EXAMPLE 55

The following compound was obtained from the trans amino compound obtained in Reference Example 16 and (R)-(–)-m-chloromandelic acid.

(1R)-1-(3-Chlorophenyl)-2-[3-(3,4-dimethoxyphenyl) cyclohexyl]aminoethanol hydrochloride 1H-NMR(CDCl$_3$) δ ppm: (free compound)1.45–1.88(8H, m), 2.49–3.06 (4H,m), 3.35–3.63(2H,br s), 3.84(3H,s), 3.86 (3H,s), 4.72(1H,br s), 6.74–6.81(3H,m), 7.19–7.26(3H,m), 7.39(1H,s).

EXAMPLE 56

The following compound was obtained from the cis amino compound obtained in Reference Example 16 and (R)-(–)-m-chloromandelic acid.

(1R)-1-(3-Chlorophenyl)-2-[3-(3,4-dimethoxyphenyl) cyclohexyl]aminoethanol

1H-NMR(CDCl$_3$) δ ppm:1.15–1.42(4H,m), 1.85–2.13 (4H,m), 2.43–2.48(1H,m), 2.65–2.73(2H,m), 2.94–2.98(1H, m), 3.84(3H,s), 3.85(3H,s), 3.84–3.85(2H,br s), 4.72(1H,d, J=7.32 Hz), 6.71–6.80 (3H,m), 7.21–7.27(3H,m), 7.36(1H, s).

EXAMPLE 57

The following compound was synthesized from the compound in Example 55, according to the method of Example 7. (2R)-4-[3-[2-(3-Chlorophenyl)-2-hydroxyethylamino] cyclohexyl]benzene-1,2-diol hydrochloride 1H-NMR(CD$_3$OD) δ ppm: (free compound)1.74–2.07 (8H,m), 2.94–3.08 (2H,m), 3.17–3.22(1H,m), 3.44–3.47 (1H,m), 4.99–5.03(1H,m), 6.62(1H,d, J=7.94 Hz), 6.72–6.75(2H,m), 7.31–7.37(3H,m), 7.48(1H,s).

EXAMPLE 58

The following compound was synthesized from the compound in Example 56, according to the method of Example 7. (2R)-4-[3-[2-(3-Chlorophenyl)-2-hydroxyethylamino] cyclohexyl]benzene-1,2-diol hydrochloride 1H-NMR(CD$_3$OD) δ ppm: (free compound)1.28–2.48 (8H,m), 3.04–3.21 (4H,m), 6.54(1H,d, J=7.93 Hz), 6.71–6.74(3H,m), 7.30–7.34(3H,m), 7.46(1H,s).

EXAMPLE 59

The following compound was synthesized from the compound of Example 57, according to the method of Example 11. (2R)-Ethyl (4-[3-[2-(3-chlorophenyl)-2-hydroxyethylamino]cyclohexyl]-2-ethoxycarbonylmethoxyphenoxy)acetate 1H-NMR(CDCl$_3$) δ ppm: (free compound)1.53(3H,t, J=7.32 Hz), 1.54(3H,t, J=7.32 Hz), 1.39–1.83(8H,m), 2.59–3.03(6H,m), 4.25(4H,q, J=7.32 Hz), 4.67(2H,s), 4.71 (2H,s), 4.65–4.71(1H,m), 6.77–6.84(3H,m), 7.20–7.30(3H, m), 7.39(1H,s).

EXAMPLE 60

(2R)-Diethyl 5-[3-[2-(3-chlorophenyl)-2-hydroxyethylamino]cyclohexyl]benzo-1,3-dioxol-2,2-dicarboxylate 1H-NMR(CDCl$_3$) δ ppm: (free compound)1.34(6H,t, J=7.32 Hz) 1.41–1.84(8H,m), 2.59–3.04(6H,m), 4.36(2H,q, J=7.32 Hz), 4.67(1H,dd, J=3.05, 9.16 Hz), 6.72–6.86(3H, m), 7.25–7.27(3H,m), 7.39(1H,s).

EXAMPLE 61

The following compound was synthesized from the compound of Example 58, according to the method of Example 11. (2R)-Diethyl 5-[3-[2-(3-chlorophenyl)-2-hydroxyethylamino]cyclohexyl]benzo-1,3-dioxol-2,2-dicarboxylate 1H-NMR(CDCl$_3$) δ ppm:(free compound)1.34(6H,t, J=7.32 Hz), 1.10–1.36(2H,m), 1.79–3.08(12H,m), 4.36(4H, q, J=7.32 Hz), 4.77(1H,dd, J=3.05, 9.16 Hz), 6.69–6.85(3H, m), 7.22–7.29(3H,m), 7.38(1H,s).

EXAMPLE 62

The following compound was synthesized from the compound of Example 60, according to the method of Example 15. Sodium (2R)-5-[3-[2-(3-chlorophenyl)-2-hydroxyethylamino]cyclohexyl]benzo-1,3-dioxol-2,2-dicarboxylate 1H-NMR(DMSO-d$_6$) δ ppm:1.06–1.72(8H,m), 2.57–2.94 (4H,m), 3.38–3.56(2H,m), 4.69(1H,br d, J=5.49 Hz), 6.52–6.67(3H,m), 7.23–7.39(4H,m)

EXAMPLE 63

The following compound was synthesized from the compound of Example 61, according to the method of Example 15. Sodium (2R)-5-[3-[2-(3-chlorophenyl)-2-hydroxyethylamino]cyclohexyl]benzo-1,3-dioxol-2,2-dicarboxylate 1H-NMR(DMSO-d6) δ ppm:1.07–1.37(4H,m), 1.73–1.96(4H,m), 2.43–2.81(4H,m), 4.67–4.69(1H,m), 6.54–6.68(3H,m), 7.25–7.38(4H,m).

EXAMPLE 64

Ethyl 3-(3-aminocyclohexyl)phenoxyacetate (8.47 g) was dissolved in ethanol (50 ml), and (R)-3-chlorostyrene oxide (4.72 g) was added prior to heating to reflux for 7.5 hours. After allowing the mixture to cool, the solvent was concentrated under reduced pressure to obtain an oily substance which was then separated and purified by silica gel column chromatography (n-hexane:ethyl acetate=1:5), to give 8.15 g of (1R)-1-(3-chlorophenyl)-2-[3-(3-ethoxycarbonylmethoxyphenyl) cyclohexylamino]ethanol (trans-H) (compound of Example 11) as an oily substance (61.8% yield).

After dissolving (1R)-1-(3-chlorophenyl)-2-[3-(3-ethoxycarbonylmethoxyphenyl) cyclohexylamino]ethanol (trans-H) (free base) (5.0 g) in ethanol (60 ml), maleic acid (1.37 g) was added, and the mixture was stirred at room temperature for 3 hours. The deposited crystals were filtered off and dried to give 2.92 g of a maleic acid salt as a white crystalline powder (51%). (maleic acid salt)

1H-NMR(CD$_3$OD) δ ppm:1.29(3H,t, J=7.32 Hz), 1.70–2.22(8H,m), 3.06–3.15(2H,m),3.25–3.26(1H,m), 3.53–3.57(1H,m), 4.24 (2H,q, J=7.32 Hz), 4.69(2H,s), 4.97–5.02(1H,m), 6.$_{26}$($_2$H,s), 6.76(1H,d, J=7.94 Hz), 6.90–6.96(2H,m), 7.25(1H,t, J=7.94 Hz), 7.35–7.37(3H,m), 7.50(1H,s).

mp.157.5–160.0 C(decomp.) Elemental analysis: as C$_{28}$H$_{34}$ClNO$_8$ Calculated: C; 61.37, H; 6.25, N; 2.56 Found: C; 61.52, H; 6.38, N; 2.45

EXAMPLE 65

The following compound was obtained from the compound of Reference Example 29 and (R)-(−)-m-chloromandelic acid, according to the method of Examples 1 to 4.

(1R)-1-(3-Chlorophenyl)-2-[3-(4-methoxyphenyl) cyclopentyl]aminoethanol hydrochloride 1H-NMR(CDCl$_3$) δ ppm:(free compound)1.38–2.36(6H, m), 2.65–2.73 (1H,m), 2.87(1H,dd, J=3.66, 12.2 Hz), 2.99 (1H,m), 3.23–3.79(3H,m), 3.79(3H,s), 4.70(1H,dd, J=3.66, 9.16 Hz), 6.85 (2H,d, J=8.55 Hz), 7.14(2H,m), 7.25(3H,s), 7.40(1H,s).

The following compounds were obtained according to the method of Example 7.

EXAMPLE 66

(2R)-4-[3-[2-(3-Chlorophenyl)-2-hydroxyethylamino]cyclopentyl]phenol (amine of starting material: trans-H form)

1H-NMR(CDCl$_3$) δ ppm:1.40–2.04(6H,m), 2.32–2.37 (1H,m), 2.68–2.84(2H,m), 2.98(1H,m), 4.73(1H,dd, J=3.66, 9.16 Hz), 6.76 (2H,d, J=8.55 Hz), 7.08(2H,d, J=8.55 Hz), 7.26(3H,s), 7.39(1H,s).

EXAMPLE 67

(2R)-4-[3-[2-(3-Chlorophenyl)-2-hydroxyethylamino]cyclopentyl]phenol (amine of starting material: trans-L form)

1H-NMR(CDCl$_3$) δ ppm:1.17–2.31(7H,m), 2.67–2.83 (2H,m), 3.12–3.31(2H,m), 4.73(1H,dd, J=3.66, 9.16 Hz), 6.74(2H,d, J=7.93 Hz), 7.02(2H,m), 7.24(3H,s), 7.36(1H,s).

EXAMPLE 68

(2R)-4-[3-[2-(3-Chlorophenyl)-2-hydroxyethylamino]cyclopentyl]phenol (amine of starting material: cis form—a mixture of cis-H and cis-L)

1H-NMR(CDCl$_3$) δ ppm:(free compound, diastereomeric mixture)
1.34–2.26(7H,m), 2.64–3.29(4H,m), 4.73(1H,d, J=8.55 Hz), 6.73 (2H,d, J=8.55 Hz), 6.89, 6.99(each 2H,d, J=8.88, 7.94 Hz), 7.21(3H,m), 7.33(1H,s).

EXAMPLE 69

The following compound was obtained using the compound of Example 66, according to the method of Example 11.

(2R)-Ethyl (4-[3-[2-(3-chlorophenyl)-2-hydroxyethylamino]cyclopentyl]phenoxy)acetate 1H-NMR(CD$_3$OD) δ ppm: (HCl salt)1.29(3H,t, J=7.32 Hz), 1.68–2.53 (7H,m), 3.06–3.32(3H,m), 3.74–3.82(1H, m), 4.24(2H,q, J=7.32 Hz), 4.66(2H,s), 4.98(1H,d, J=9.77 Hz), 6.87(2H, d, J=7.32 Hz), 7.20 (2H,m), 7.37(3H,s), 7.50(1H,s).

EXAMPLE 70

The following compound was obtained using the compound of Example 67, according to the method of Example 11.

(2R)-Ethyl (4-[3-[2-(3-chlorophenyl)-2-hydroxyethylamino]cyclopentyl]phenoxy)acetate 1H-NMR(CD$_3$OD) δ ppm: (HCl salt)1.29(3H,t, J=7.32 Hz), 1.76–2.53 (7H,m), 3.06–3.32(3H,m), 3.74(1H,m), 4.24 (2H,q, J=7.32 Hz), 4.66(2H,s), 4.98(1H,d, J=9.77 Hz), 6.87 (2H,d, J=9.16 Hz), 7.19 (2H,d, J=9.16 Hz), 7.24(3H,s), 7.37(1H,s).

The following compounds were obtained according to the methods of Examples 65 to 69.

EXAMPLE 71

(1R)-1-(3-Chlorophenyl)-2-[3-(4-methoxyphenyl) cyclopentyl]aminoethanol

1H-NMR(CDCl$_3$) δ ppm: (free compound, diastereomer mixture) 1.44–2.15(12H,m), 2.35(1H,m), 2.68–2.87(4H,m), 3.00(1H,m), 3.22–3.37(4H,m), 3.78(6H,s), 4.77(2H,dd, J=3.66, 5.49 Hz), 6.84 (4H,d, J=8.55 Hz), 7.14(4H,d, J=7.94 Hz), 7.26(6H,s), 7.39(2H,s).

EXAMPLE 72

The diastereomeric compound of Example 73,(2R)-ethyl (4-[3-[2-(3-chlorophenyl)-2-hydroxyethylamino] cyclopentyl]phenoxy)acetate 1H-NMR(CDCl$_3$) δ ppm: (free compound)1.30(3H,t, J=7.32 Hz), 1.33–2.34(6H,m), 2.61–3.35(6H,m), 4.27(2H,q, J=7.32 Hz), 4.59(2H,s),4.66(1H,dd, J=3.66, 8.54 Hz), 6.83 (2H,d, J=8.54 Hz), 7.13(2H,d, J=8.54 Hz), 7.17(3H,s), 7.39 (1H,s).

EXAMPLE 73

The diastereomeric compound of Example 72,(2R)-ethyl (4-[3-[2-[3-chlorophenyl)-2-hydroxyethylamino] cyclopentyl]phenoxy)acetate 1H-NMR(CDCl$_3$) δ ppm: (free compound)1.30(3H,t, J=7.32 Hz), 1.36–2.37(6H,m), 2.61–3.25(6H,m), 4.27(2H,q, J=7.32 Hz), 4.59(2H,s), 4.68(1H,dd, J=3.66, 5.49 Hz), 6.83 (2H,d, J=8.54 Hz), 7.11(2H,d, J=8.54 Hz), 7.25(3H,s), 7.38 (1H,s).

EXAMPLE 74

The following compound was obtained using the compound of Example 68, according to the method of Example 11.

(2R)-Diethyl (4-[3-[2-(3-chlorophenyl)-2-hydroxyethylamino]cyclopentyl]phenoxy) malonate 1H-NMR(CDCl$_3$) δ ppm: (free compound)1.30(6H,t, J=7.32 Hz), 1.39–2.33(7H,m), 2.62–2.72(3H,m), 2.92–3.45 (3H,m), 4.31 (4H,q, J=7.32 Hz), 4.68(1H,d, J=5.49 Hz), 5.16(1H,s), 6.89 (2H,d, J=8.54 Hz), 7.13(2H,d, J=8.54 Hz), 7.25(3H,s), 7.38(1H,s).

EXAMPLE 75

The following compound was obtained according to the method of Example 47.

(2R)-2-[4-[3-[2-(3-Chlorophenyl)-2-hydroxyethylamino] cyclopentyl]phenoxy]-N-(2-methoxyethyl)acetamide 1H-NMR(CDCl$_3$) δ ppm: (free compound)1.36–2.33(7H, m), 2.69–2.94 (5H,m), 3.26–3.36(1H,m), 3.34(3H,s), 3.48–3.52(4H,m), 4.46(2H,m), 4.68(1H,d, J=5.65 Hz), 6.85 (2H,d, J=8.55 Hz), 6.94 (1H,br s), 7.13–7.25(5H,m), 7.38 (1H,s).

EXAMPLE 76

The following compounds were obtained from the compound of Reference Example 38 and (R)-(–)-m-chloromandelic acid, according to the method of Examples 1 to 4.

(1R)-1-(3-Chlorophenyl)-2-[3-(3-methoxyphenyl) cyclopentyl]aminoethanol hydrochloride (diastereomer A)

1H-NMR(CDCl$_3$) δ ppm: (free compound)1.46–1.62(2H, m), 1.79–2.38 (4H,m), 2.65–2.72(1H,m), 2.87–3.34(3H,m), 3.67(2H,br s), 3.78 (3H,s), 4.74(1H,dd, J=3.05, 9.16 Hz), 6.71–6.83(3H,m), 7.16–7.24 (4H,m), 7.38(1H,s).

(1R)-1-(3-chlorophenyl)-2-[3-(3-methoxyphenyl) cyclopentyl]aminoethanol hydrochloride (diastereomer B)

1H-NMR(CDCl$_3$) δ ppm: (free compound) 1.46–1.62 (2H,m), 1.79–2.38 (4H,m), 2.67–2.70(1H,m), 2.87–3.34 (3H,m), 3.49(2H,brs), 3.78(3H,s), 4.73(1H,d, J=6.10 Hz), 6.70–6.83(3H,m), 7.16–7.23 (4H,m), 7.37(1H,s).

EXAMPLE 77

The following compounds were obtained from the compound of Example 76, according to the method of Example 7.

(2R)-3-[3-[2-(3-Chlorophenyl)-2-hydroxyethylamino] cyclopentyl]phenol (diastereomer A)

1H-NMR(CD$_3$OD) δ ppm:1.72–2.44(6H,m), 2.94–3.32 (3H.m), 3.60–3.69(1H,m), 5.00(1H,s), 6.62–6.74(3H,m), 7.06–7.12(1H,m), 7.31–7.36(3H,m), 7.49(1H,s).

(2R)-3-[3-[2-(3-Chlorophenyl)-2-hydroxyethylamino] cyclopentyl]phenol (diastereomer B)

1H-NMR(CD$_3$OD) δ ppm:1.52–2.44(6H,m), 2.82–3.27 (3H,m), 3.45–3.52(1H,m), 4.89(1H,d, J=9.16 Hz), 6.61–6.72(3H, m), 7.06–7.11 (1H,m), 7.29–7.31 (3H,m), 7.45 (1H, s)

EXAMPLE 78

The following compounds were obtained from the compound of Example 77, according to the method of Example 11.

(2R)-Ethyl (3-[3-[2-(3-Chlorophenyl)-2-hydroxyethylamino]cyclopentyl]phenoxy) acetate hydrochloride (diastereomer A)

1H-NMR(CDCl$_3$) δ ppm: (free compound)1.29(3H,t, J=7.32 Hz), 1.50–2.37(7H,m), 2.68–2.76(1H,m), 2.90–3.29 (3H,m), 3.95 (2H,brs), 4.26(2H,q, J=7.32 Hz), 4.58(2H,s), 4.78(1H,d, J=6.10 Hz), 6.69(1H,d, J=7.93 Hz), 6.78–6.88 (2H,m), 7.15–7.26 (4H,m), 7.38 (1H, s).

(2R)-Ethyl (3-[3-[2-(3-chlorophenyl)-2-hydroxyethylamino]cyclopentyl]phenoxy)acetate (diastereomer B)

1H-NMR(CDCl$_3$) δ ppm: (free compound)1.30(3H,t, J=7.32 Hz), 1.43–2.37(7H,m), 2.67–2.75(1H,m), 2.94–3.28 (5H,m), 4.27(2H,q, J=7.32 Hz), 4.60(2H,s), 4.75(1H,d, J=5.49 Hz), 6.70 (1H,d, J=7.93 Hz), 6.68–6.89(2H,m), 7.17–7.26(4H,m), 7.39 (1H,s).

The following compounds were obtained from the compound of Reference Example 33 and (R)-(–)-m-chloromandelic acid, according to the methods of Examples 1 to 4.

EXAMPLE 79

(1R)-1-(3-Chlorophenyl)-2-[3-(4-methoxyphenyl) cyclopentylmethyl]aminoethanol

1H-NMR(CDCl$_3$) δ ppm:(free compound)1.20–2.30(7H, m), 2.58–3.06 (7H,m), 3.78(3H,s), 4.67(1H,dd, J=3.66, 8.55 Hz), 6.83(2H,d, J=8.55 Hz), 7.14(2H,d, J=8.55 Hz), 7.24 (3H,m), 7.38(1H,s).

EXAMPLE 80

The following compound was obtained from the compound of Example 79, according to the method of Example 7.

(2R)-4-[3-[2-(3-Chlorophenyl)-2-hydroxyethylaminomethyl]cyclopentyl]phenol

1H-NMR(DMSO-d$_6$) δ ppm:1.18–2.33(8H,m), 2.70–3.00 (5H,m), 4.79(1H,dd, J=3.05, 8.55 Hz), 6.66(2H,d, J=8.55 Hz), 7.01(2H,d, J=8.55 Hz), 7.33(3H,m), 7.42(1H,s).

EXAMPLE 81

The following compound was obtained from the compound of Example 80, according to the method of Example 11.

(2R)-Ethyl (4-[3-[2-(3-chlorophenyl)-2-hydroxyethylaminomethyl]cyclopentyl]phenoxy)acetate hydrochloride 1H-NMR(CDCl$_3$) δ ppm: (free compound)1.28–2.30(7H, m), 2.65–2.73 (3H,m), 2.93–3.01(2H,m), 3.64(2H,brs), 4.25 (2H,q, J=7.32 Hz), 4.57(2H,s), 4.75(1H,d, J=6.10 Hz), 6.82 (2H,d, J=8.55 Hz), 7.12(2H, d, J=8.55 Hz), 7.22(3H,m), 7.37(1H,s).

EXAMPLE 82

(2R)-Diethyl [4-[3-[2-(3-chlorophenyl)-2-hydroxyethylaminomethyl]cyclopentyl]phenoxy] malonate hydrochloride 1H-NMR(CDCl$_3$) δ ppm: (free compound) 1.29(6H,t, J=7.32 Hz), 1.32–2.61(7H,m), 2.67–2.75(3H,m), 2.90–2.96 (2H,m), 3.62(2H,brs), 4.30(4H,q, J=7.32 Hz), 4.76(1H,d, J=6.10 Hz), 5.16(1H,s), 6.88(2H,d, J=7.94 Hz), 7.13(2H,d, J=7.94 Hz), 7.23(3H, s), 7.38(1H,s).

EXAMPLE 83

The following compound was obtained from the compound of Example 81, according to the method of Example 47.

(2R)-2-[4-[3-[2-(3-Chlorophenyl)-2-hydroxyethylaminomethyl]cyclopentyl]phenoxy]-N-(2-methoxyethyl)acetamide 1H-NMR(CDCl$_3$) δ ppm: (free compound)1.19–2.31(7H, m), 2.58–2.72 (3H,m), 2.83–3.06(4H,m), 3.33(3H,s), 3.47–3.52(4H,m), 4.45(2H,s), 4.68(1H,dd, J=3.66, 9.16 Hz), 6.83(2H,d, J=8.55 Hz), 6.99(1H,brs), 7.15(2H,d, J=8.55 Hz), 7.23(3H,s), 7.38(1H,s).

EXAMPLE 84

(R)-2-Amino-1-(3-chlorophenyl) ethanol (770 mg) and ethyl 4-(3-oxocyclopentyl) benzoate (1.15 g) were dissolved in ethanol (60 ml), and platinum oxide (80 mg) and acetic acid (2.8 ml) were added thereto. After substituting the reaction vessel with hydrogen gas, reducing amination reaction was carried out for 30 minutes at normal pressure and room temperature. After the reaction, the catalyst was filtered off and the solvent was distilled off under reduced pressure to produce an oily substance, and upon addition of saturated bicarbonate water to achieve alkalinity, extraction was performed with ethyl acetate.

After washing the organic layer with water and drying with anhydrous magnesium sulfate, the solvent was distilled off under reduced pressure to produce orange crystals which were then purified by silica gel column chromatography (chloroform→chloroform:ethanol=20:1). The resulting crystals were further washed with n-hexane:ethyl acetate= 2:1 to give 314 mg of ethyl (2R)-4-[3-[2-(3-chlorophenyl)-2-hydroxyethylamino]cyclohexyl]benzoate (16.4%).

1H-NMR(CDCl$_3$) δ ppm:1.38(3H,t, J=7.32 Hz), 1.45–2.20(7H,m), 2.37–2.46(1H,m), 2.65–2.73(1H,m), 2.93–3.23(3H,m), 4.36 (2H,q, J=7.32 Hz), 4.68(1H,dd, J=3.05, 8.54 Hz), 7.26–7.31(5H,m), 7.39(1H,s), 7.79(2H,d, J=8.55 Hz).

The following are preparation examples for the compounds of the invention.

Tablets: The compound of Example 11 (5 mg), microcrystalline cellulose (40 mg), dry corn starch (40 mg), lactose (100 mg) and magnesium stearate (5 mg) are combined according to a common method and formed into granules, which are then compression molded to make tablets containing 5 mg of the active substance.

Capsules: The compound of Example 15 (10 mg) and lactose (120 mg) are combined, and the mixture is filled into common hard gelatin capsules to prepare capsules containing 10 mg of the active substance.

Industrial Applicability

As explained above, the compounds of the present invention have a potent β3 adrenergic stimulating effect and high β3 adrenergic receptor selectivity, which not only render them effective as prophylactics and/or treatments for gastrointestinal diseases accompanying smooth muscle hypersthenia (for example, irritable bowel syndrome, acute and chronic diarrhea, etc.) as well as improvement of symptoms associated with gastric ulcer, duodenal ulcer, gastritis, enteritis, cholecystitis and the like, such as abdominal pain, nausea, vomiting and epigastric discomfort, but also allow their use as therapeutic agents for diseases for which stimulation of β3 adrenergic receptors is believed to be advantageous, for example as antiobestic drugs, antidiabetic drugs or antidepressive drugs.

In addition, because they exhibit a stronger relaxing effect on the bladder detrusor muscle (smooth muscle) than the β2 adrenergic agonist clenbuterol hydrochloride, the compounds of the present invention are useful as selective β3 adrenergic receptor agonists, for the prevention and/or treatment of pollakisuria and urinary incontinence, including nervous pollakisuria neurogenic bladder dysfunction, bladder instability and abdominal pressure anischuria.

Furthermore, because the compounds of the present invention have a weak stimulating effect on β1 and β2 adrenergic receptors, they have an advantage of few side effects caused by β1 and β2 action (for example, increased cardiac rate or tremor).

What is claimed is:

1. A phenylethanolamine compound represented by general formula [I]:

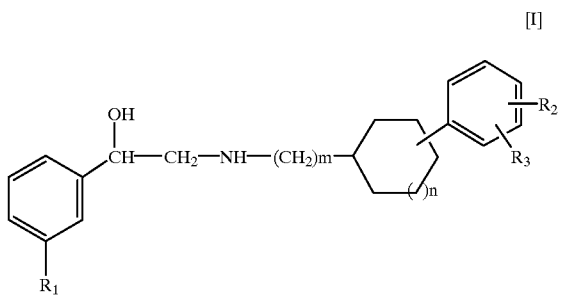

(where $R_1$ represents hydrogen or halogen; $R_2$ represents hydrogen, hydroxy, lower alkoxy, lower alkoxy substituted with one or two lower alkoxycarbonyl or carboxy groups, lower alkoxy substituted with lower alkylaminocarbonyl which may be substituted with lower alkoxy, lower alkoxy substituted with cyclic aminocarbonyl of 4 to 6 carbon atoms, lower alkoxycarbonyl or carboxy; $R_3$ represents hydrogen, hydroxy, lower alkoxy or lower alkoxy substituted with one or two lower alkoxycarbonyl or carboxy groups; $R_2$ and $R_3$ may be bonded to each other to form methylenedioxy substituted with carboxy or lower alkoxycarbonyl; and m and n are 0 or 1), or a pharmacologically acceptable salt thereof.

2. A compound according to claim 1, wherein $R_1$ is a chlorine atom, $R_2$ represents hydroxy, lower alkoxy, methoxy substituted with one or two lower alkoxycarbonyl or carboxy groups, methoxy substituted with lower alkylaminocarbonyl which may be substituted with lower alkoxy, or methoxy substituted with cyclic aminocarbonyl of 4 to 6 carbon atoms; $R_3$ represents hydrogen, hydroxy, lower alkoxy or methoxy substituted with one or two lower alkoxycarbonyl or carboxy groups; $R_2$ and $R_3$ may be bonded to each other to form methylenedioxy substituted with carboxy or lower alkoxycarbonyl; m is 0 and n is 1.

3. A compound according to claim 2, wherein $R_1$ is a chlorine atom, $R_2$ is methoxy substituted with carboxy or lower alkoxy carbonyl, m is 0 and n is 1.

4. A compound wherein the asymmetrical carbon to which the primary hydroxyl group of the 1-phenyl-2-(3-phenylcyclohexylamino) ethanol according to claim 2 is attached has the absolute configuration (R).

5. (1R)-1-(3-chlorophenyl)-2-[(1R),(3R)-3-(3-ethoxycarbonylmethoxyphenyl)cyclohexylamino]ethanol, (1R)-1-(3-chlorophenyl)-2-[(1S),(3S)-3-(3-ethoxycarbonylmethoxyphenyl)cyclohexylamino]ethanol, (1R)-1-(3-chlorophenyl)-2-[(1R),(3R)-3-(3-carboxymethoxyphenyl) cyclohexylamino]ethanol, (1R)-1-(3-chlorophenyl)-2-[(1S),(3S)-3-(3-carboxymethoxyphenyl)cyclohexylamino]ethanol, or a pharmacologically acceptable salt thereof.

6. A process for producing a phenylethanolamine compound represented by general formula [I]:

[I]

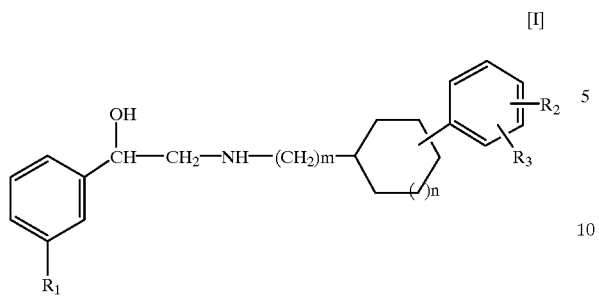

(where $R_1$ represents hydrogen or halogen; $R_2$ represents hydrogen, hydroxy, lower alkoxy, lower alkoxy substituted with one or two lower alkoxycarbonyl or carboxy groups, lower alkoxy substituted with lower alkylaminocarbonyl which may be substituted with lower alkoxy, lower alkoxy substituted with cyclic aminocarbonyl of 4 to 6 carbon atoms, lower alkoxycarbonyl or carboxy; $R_3$ represents hydrogen, hydroxy, lower alkoxy or lower alkoxy substituted with one or two lower alkoxycarbonyl or carboxy groups; $R_2$ and $R_3$ may be bonded to each other to form methylenedioxy substituted with carboxy or lower alkoxycarbonyl; and m and n are 0 or 1), or a pharmacologically acceptable salt thereof, which process involves reacting a compound of formula [II]

[II]

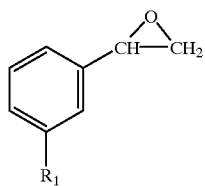

with a compound of formula [III] or its salt,

[III]

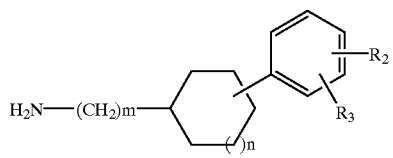

to produce a compound of formula [I] (where $R_1$, $R_2$, $R_3$, m and n have the same definitions given above), or a pharmacologically acceptable salt thereof.

7. A production process which comprises reacting a compound of formula [IV]

[IV]

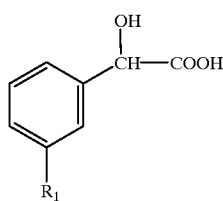

(where $R_1$ represents hydrogen or halogen), with a compound of formula [III']

[III']

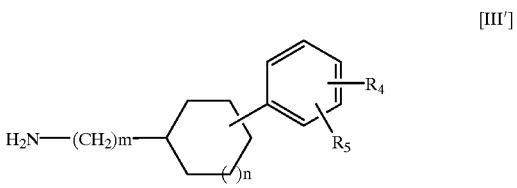

(where $R_4$ and $R_5$ each represents hydrogen, hydroxy or lower alkyl; and m and n are 0 or 1), or its salt, to produce a compound of formula [V]

[V]

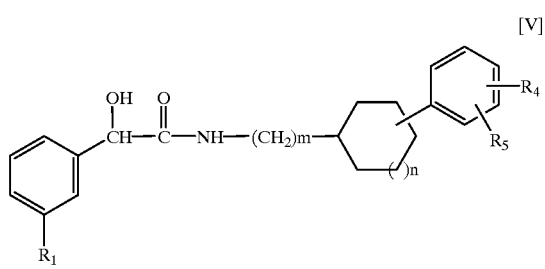

(where $R_1$, $R_4$, $R_5$, m and n have the same definitions given above), and then reducing the amide group of the compound of formula [V] to produce a compound of formula [VI]

[VI]

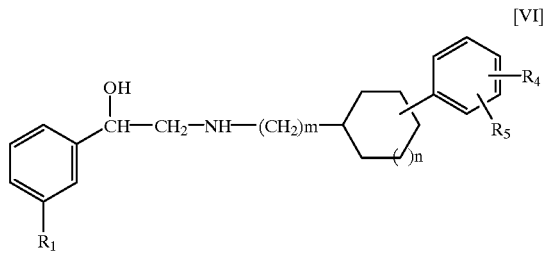

(where $R_1$, $R_4$, $R_5$, m and n have the same definitions given above), or a pharmacologically acceptable salt thereof.

8. A production process which comprises protecting the amino group of a compound of formula [VII]

[VII]

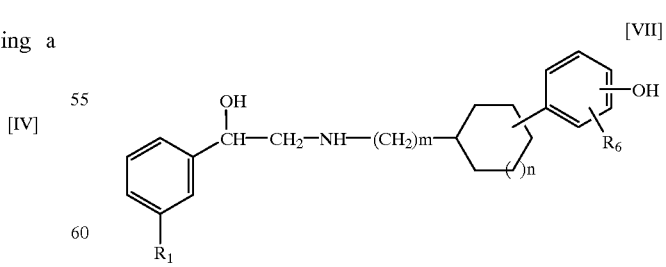

(where $R_1$ represents hydrogen or halogen; $R_6$ represents hydrogen or hydroxy; and m and n are 0 or 1), with a protecting group for making a compound of formula [VIII]

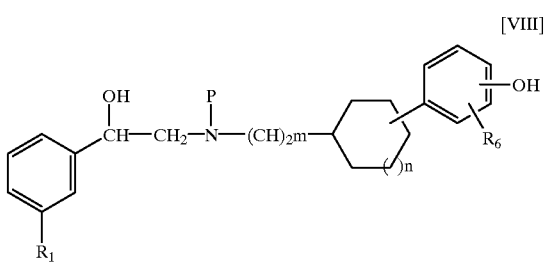

[VIII]

(where $R_1$, $R_6$, m and n have the same definitions given above; and P represents an N-protecting group), and then reacting the compound of formula [VIII] with a compound of formula [IX] or [IX']

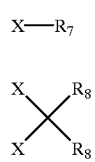

[IX]

[IX']

(where $R_7$ represents lower alkyl substituted with one or two lower alkoxy carbonyl groups; $R_8$ represents lower alkoxy carbonyl; and X represents an acid residue), and subsequently removing the N-protecting group to produce a compound of formula [X]

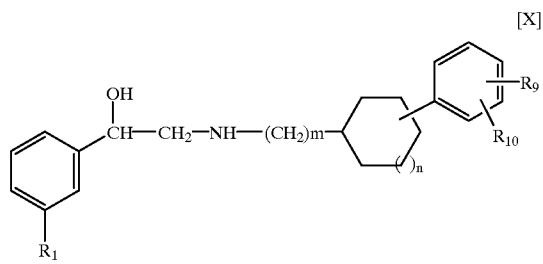

[X]

(where $R_1$, m and n have the same definitions given above; $R_9$ represents lower alkoxy substituted with one or two lower alkoxy carbonyl groups; $R_{10}$ represents hydrogen or lower alkoxy substituted with one or two lower alkoxy carbonyl groups; and $R_9$ and $R_{10}$ may be bonded to each other to form methylene dioxy substituted with lower alkoxy carbonyl), or a pharmacologically acceptable salt thereof.

9. A production process which comprises subjecting a compound of formula [X]

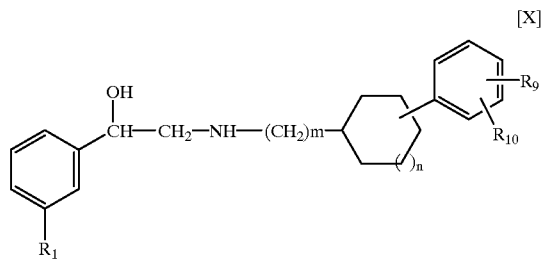

[X]

(where $R_1$ represents hydrogen or halogen; $R_9$ represents lower alkoxy substituted with one or two lower alkoxy carbonyl groups; $R_{10}$ represents hydrogen or lower alkoxy substituted with one or two lower alkoxy carbonyl groups; $R_9$ and $R_{10}$ may be bonded to each other to form a methylene dioxy substituted with lower alkoxy carbonyl; and m and n are 0 or 1), or its salt, to de-esterification reaction to produce a compound of formula [XI]

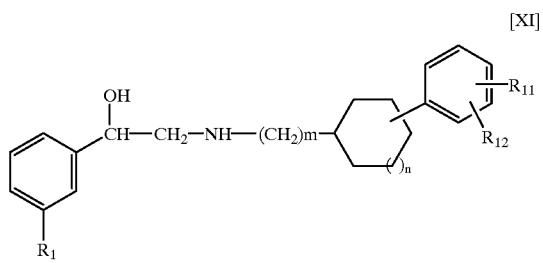

[XI]

(where $R_1$, m and n have the same definitions given above; $R_{11}$ represents lower alkoxy substituted with one or two carboxy groups; $R_{12}$ represents hydrogen or lower alkoxy substituted with one or two carboxy groups; and $R_{11}$ and $R_{12}$ may be bonded to each other to form methylene dioxy substituted with carboxy), or a pharmacologically acceptable salt thereof.

10. A production process which comprises reacting a compound of formula [X]

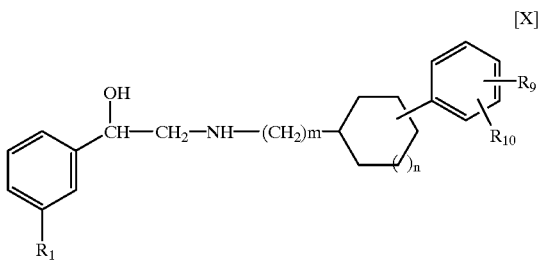

[X]

(where $R_1$ represents hydrogen or halogen; $R_9$ represents lower alkoxy substituted with one or two lower alkoxy carbonyl groups; $R_{10}$ represents hydrogen; and m and n are 0 or 1), or its salt, or a compound of formula [XI]

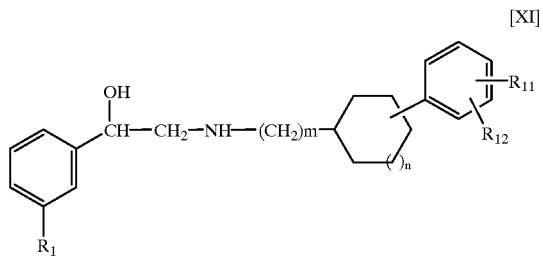

[XI]

(where $R_1$, m and n have the same definitions given above; $R_{11}$ represents lower alkoxy substituted with one or two carboxy groups; and $R_{12}$ represents hydrogen), or its salt, with a lower alkyl amine which may be substituted with lower alkoxy, or a cyclic amine of 4 to 6 carbon atoms, to produce a compound of formula [XII]

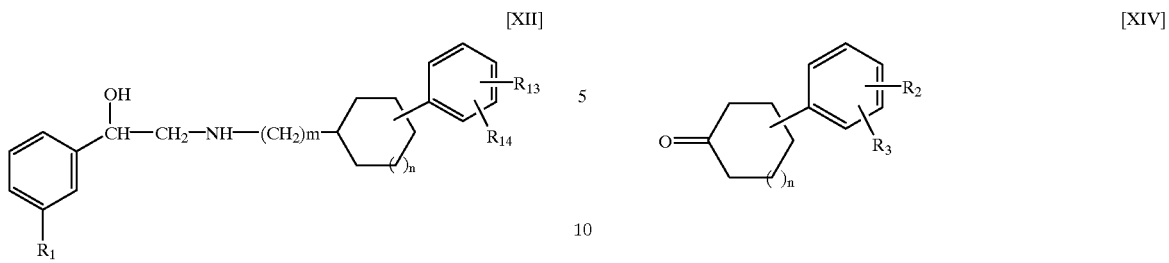

[XII]

(where $R_1$, m and n have the same definitions given above; $R_{13}$ represents lower alkoxy substituted with a lower alkyl amino carbonyl group which may be substituted with one or two lower alkoxy groups or lower alkoxy substituted with a cyclic amino carbonyl group of 4 to 6 carbon atoms; and $R_{14}$ represents hydrogen), or a pharmacologically acceptable salt thereof.

11. A production process which comprises producing a compound of formula [XV]

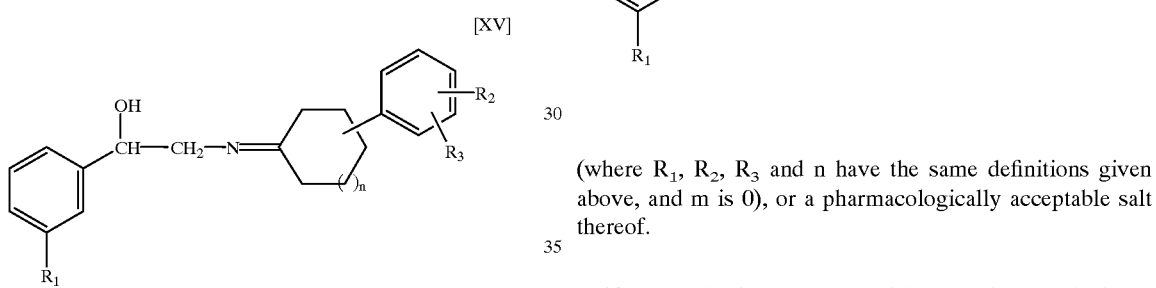

[XV]

(where $R_1$ represents hydrogen or halogen; $R_2$ represents hydrogen, hydroxy, lower alkoxy, lower alkoxy substituted with one or two lower alkoxy carbonyl or carboxy groups, lower alkoxy substituted with lower alkyl amino carbonyl which may be substituted with lower alkoxy, lower alkoxy substituted with cyclic amino carbonyl of 4 to 6 carbon atoms, lower alkoxy carbonyl or carboxy; $R_3$ represents hydrogen, hydroxy, lower alkoxy or lower alkoxy substituted with one or two lower alkoxy carbonyl or carboxy groups; $R_2$ and $R_3$ may be bonded with each other to form methylene dioxy substituted with carboxy or lower alkoxy carbonyl; and n is 0 or 1), by reacting a compound of formula [XIII]

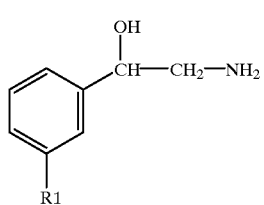

[XIII]

(where $R_1$ has the same definition given above), with a compound of formula [XIV]

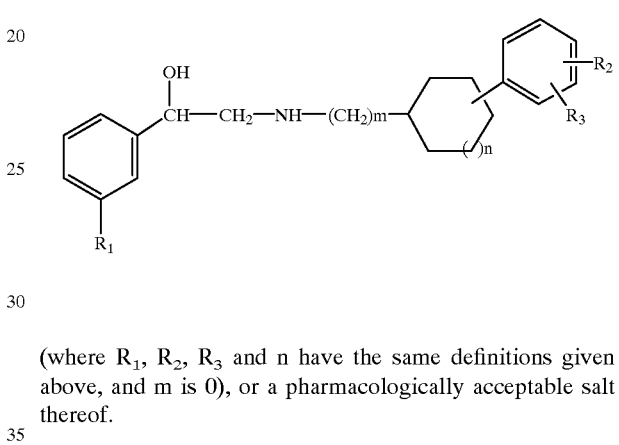

[XIV]

(where $R_2$, $R_3$ and n have the same definitions given above), and then reducing the resulting imino group of the compound of formula [XV] to produce a compound of formula [I]

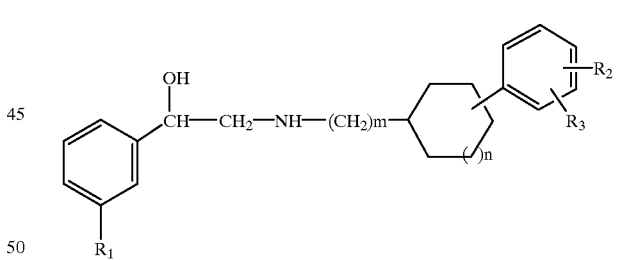

[I]

(where $R_1$, $R_2$, $R_3$ and n have the same definitions given above, and m is 0), or a pharmacologically acceptable salt thereof.

12. A production process which comprises producing a compound of formula [I]

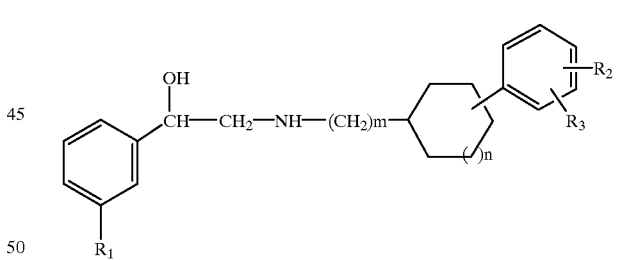

[I]

(where $R_1$ represents hydrogen or halogen; $R_2$ represents hydrogen, hydroxy, lower alkoxy, lower alkoxy substituted with one or two lower alkoxy carbonyl or carboxy groups, lower alkoxy substituted with lower alkyl amino carbonyl which may be substituted with lower alkoxy, lower alkoxy substituted with cyclic amino carbonyl of 4 to 6 carbon atoms, lower alkoxy carbonyl or carboxy; $R_3$ represents hydrogen, hydroxy, lower alkoxy or lower alkoxy substituted with one or two lower alkoxy carbonyl or carboxy groups; $R_2$ and $R_3$ may be bonded with each other to form methylene dioxy substituted with carboxy or lower alkoxy carbonyl; m is 0; and n is 0 or 1), or a pharmacologically acceptable salt thereof, from a compound of formula [XIII]

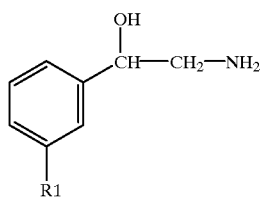

(where $R_1$ has the same definition given above), and a compound of formula [XIV]

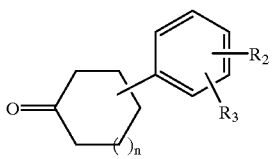

(where $R_2$, $R_3$ and n have the same definitions given above), by direct catalytic hydrogen reduction reaction.

13. A production process which comprises subjecting a compound of formula [XVI]

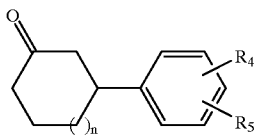

(where $R_4$ and $R_5$ each represents hydrogen, hydroxy or lower alkoxy; and n is 1), to catalytic reduction in the presence of a compound of formula [XVII]

(where $R_{15}$ represents lower alkyl substituted with aryl), and Raney nickel, to predominantly obtain a compound of formula [XVIII]

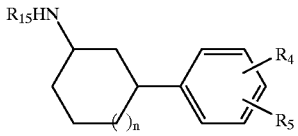

(where $R_4$, $R_5$, $R_{15}$ and n have the same definitions given above), or its salt, having the amino group and phenyl group in a trans configuration, and then subjecting the compound of formula [XVIII] to catalytic hydrogen reduction in the presence of a reducing agent to obtain a compound of formula [XIX]

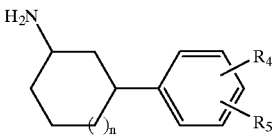

(where $R_4$, $R_5$ and n have the same definition given above), or a pharmacologically acceptable salt thereof.

14. A compound of formula [V]

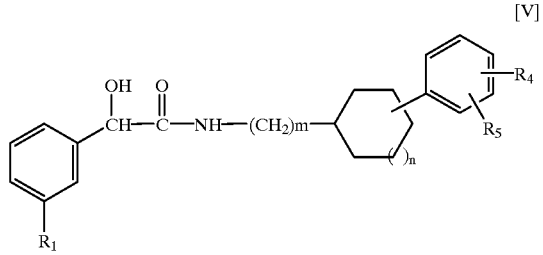

(where $R_1$ represents hydrogen or halogen; $R_4$ and $R_5$ each represents hydrogen, hydroxy or lower alkoxy; and m and n are 0 or 1).

15. A compound of formula [VIII]

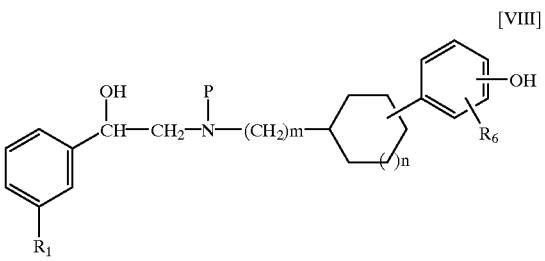

(where $R_1$ represents hydrogen or halogen; $R_6$ represents hydrogen or hydroxy; P represents an N-protecting group; and m and n are 0 or 1).

16. A compound of formula [XV]

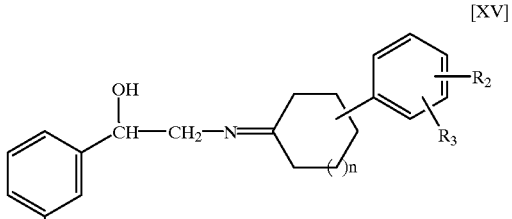

(where $R_1$ represents hydrogen or halogen; $R_2$ represents hydrogen, hydroxy, lower alkoxy, lower alkoxy substituted with one or two lower alkoxy carbonyl or carboxy groups, lower alkoxy substituted with lower alkyl amino carbonyl which may be substituted with lower alkoxy, lower alkoxy substituted with cyclic amino carbonyl of 4 to 6 carbon atoms, lower alkoxy carbonyl or carboxy; $R_3$ represents hydrogen, hydroxy, lower alkoxy or lower alkoxy substituted with one or two lower alkoxy carbonyl or carboxy groups; $R_2$ and $R_3$ may be bonded with each other to form methylene dioxy substituted with carboxy or lower alkoxy carbonyl; and n is 0 or 1).

17. A compound of formula XVIII

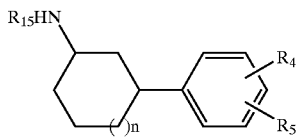

[XVIII]

(where $R_4$ and $R_5$ each represents hydrogen, halogen or lower alkoxy; $R_{15}$ represents lower alkyl substituted aryl; and n is 1) or its salt.

18. A compound of formula XIX

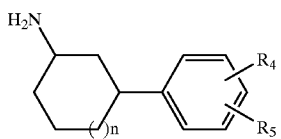

[XIX]

(where $R_4$ and $R_5$ each represents hydrogen, halogen or lower alkoxy; and n is 1), or its salt.

19. A pharmaceutical composition comprising a compound of claim 1 together with a pharmaceutically acceptable carrier or excipient.

20. A method of treating accelerated or spasmodic gastrointestinal motility in a human or animal comprising administering thereto an effective dose of a compound of claim 1.

21. A method of treating dysuria in a human or animal comprising administering thereto an effective dose of a compound of claim 1.

22. A method of treating pollakisuria in a human or animal comprising administering thereto an effective dose of a compound of claim 1.

23. A method of treating urinary incontinence in a human or animal comprising administering thereto an effective dose of a compound of claim 1.

24. A method of treating obesity in a human or animal comprising administering thereto an effective dose of a compound of claim 1.

25. A method of treating diabetes in a human or animal comprising administering thereto an effective dose of a compound of claim 1.

* * * * *